(12) United States Patent
Fung et al.

(10) Patent No.: US 8,465,929 B2
(45) Date of Patent: Jun. 18, 2013

(54) BIOMARKERS FOR OVARIAN CANCER

(75) Inventors: Eric T. Fung, Los Altos, CA (US); Frederick R. Ueland, Lexinton, KY (US); J. R. van Nagell, Lexington, KY (US); Paul D. Depriest, Versailles, KY (US); Andre T. Baron, Lexington, KY (US)

(73) Assignees: Vermillion, Inc., Austin, TX (US); The University of Kentucky Research Foundation, Lexington, KY (US)

( * ) Notice: Subject to any disclaimer, the term of this patent is extended or adjusted under 35 U.S.C. 154(b) by 400 days.

(21) Appl. No.: 11/922,652

(22) PCT Filed: Jun. 23, 2006

(86) PCT No.: PCT/US2006/024693
§ 371 (c)(1),
(2), (4) Date: Dec. 15, 2009

(87) PCT Pub. No.: WO2007/002535
PCT Pub. Date: Jan. 4, 2007

(65) Prior Publication Data
US 2010/0105067 A1    Apr. 29, 2010

Related U.S. Application Data

(60) Provisional application No. 60/693,755, filed on Jun. 24, 2005, provisional application No. 60/785,031, filed on Mar. 22, 2006.

(51) Int. Cl.
    *G01N 33/53*    (2006.01)

(52) U.S. Cl.
    USPC .................................................. 435/7.1

(58) Field of Classification Search
    None
    See application file for complete search history.

(56) References Cited

U.S. PATENT DOCUMENTS

| 7,510,842 B2 * | 3/2009 | Podust et al. ............... 435/7.1 |
| 7,605,003 B2 * | 10/2009 | Chan et al. ................ 436/178 |
| 2003/0087250 A1 * | 5/2003 | Monahan et al. ............... 435/6 |
| 2005/0059013 A1 * | 3/2005 | Chan et al. ................... 435/6 |

OTHER PUBLICATIONS

Scheffer et al (Laboratory Investigation, Apr. 2002, 82:515-518).*
Alexe G et al. "Ovarian cancer detection by logical analysis of proteomic data.Proteomics." Mar. 2004;4(3):766-83.
Ott HW et al. "Calgranulins in cystic fluid and serum from patients with ovarian carcinomas." Cancer Res. Nov. 1, 2003;63(21):7507-14.
International Search Report dated Jul. 19, 2007, mailed Sep. 20, 2007 issued for Application No. PCT/US2006/24693.
Berbee et al., "Severe hypertriglyceridemia in human APOC1 transgenic mice is caused by apoC-I-induced inhibition of LPL", Journal of Lipid Research, Feb. 2005, vol. 46, No. 2, p. 297-306.

* cited by examiner

*Primary Examiner* — Laura B Goddard
(74) *Attorney, Agent, or Firm* — Melissa Hunter-Ensor; Elbert C. Chiang; Saul Ewing LLP

(57) ABSTRACT

The present invention provides protein-based biomarkers and biomarker combinations that are useful in qualifying ovarian cancer status in a patient. In particular, the biomarkers of this invention are useful to classify a subject sample as ovarian cancer, ovarian cancer of low malignant potential, benign ovarian disease or other malignant condition. The biomarkers can be detected by SELDI mass spectrometry.

19 Claims, 1 Drawing Sheet

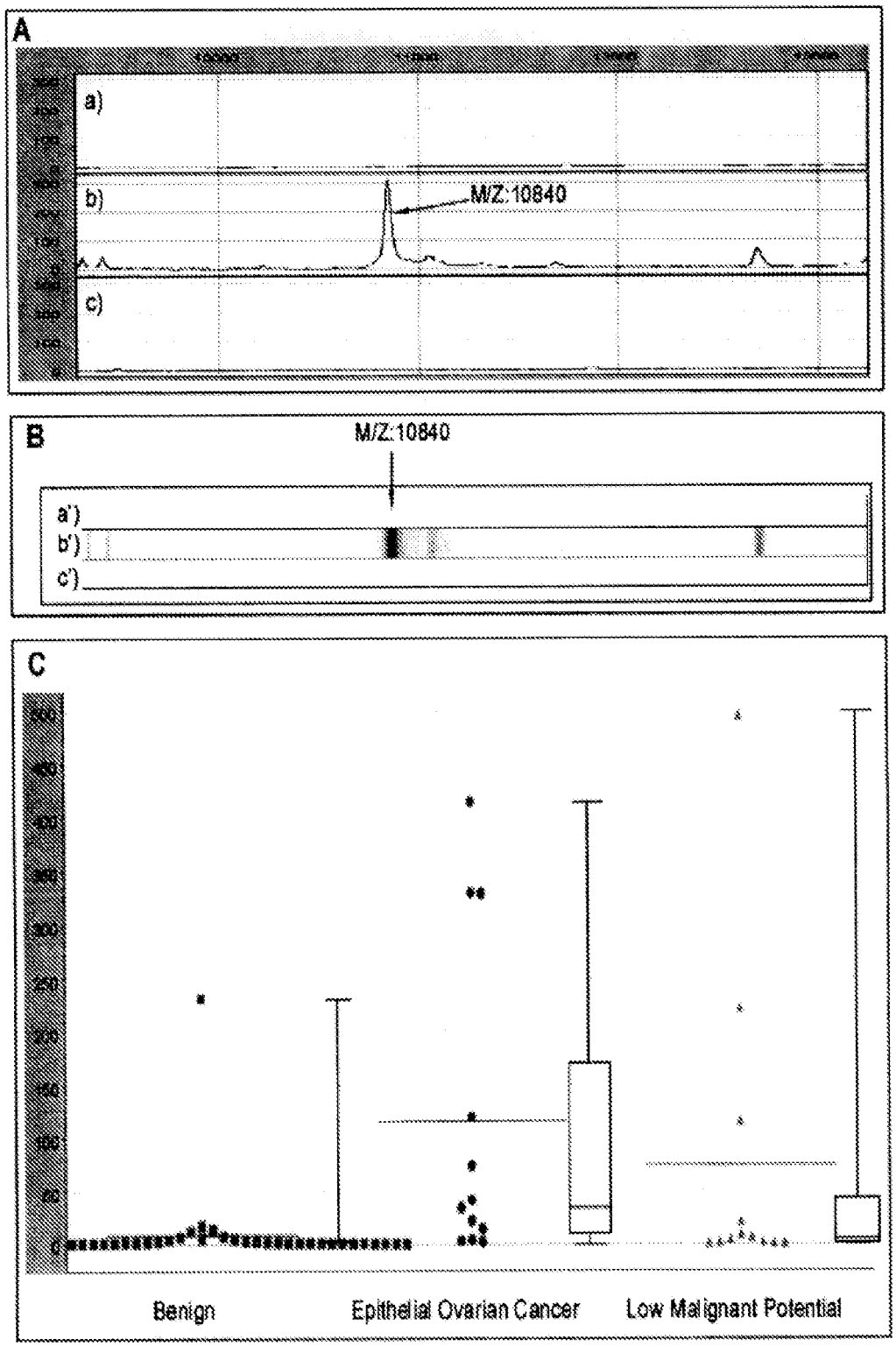

BIOMARKERS FOR OVARIAN CANCER

CROSS-REFERENCE TO RELATED CASES

This case is related to U.S. Provisional Patent Application Nos. 60/693,755, filed on Jun. 24, 2005, and 60/785,031, filed on Mar. 22, 2006, the teachings of which are incorporated herein by reference.

FIELD OF THE INVENTION

This invention relates generally to clinical diagnostics and, in particular, to clinical diagnostics for ovarian cancer.

BACKGROUND OF THE INVENTION

Ovarian cancer is among the most lethal gynecologic malignancies in developed countries. Annually, in the United States alone, approximately 23,000 women are diagnosed with the disease and almost 14,000 women die from it. (Jamal et al., *CA Cancer J. Clin.*, 52:23-47 (2002)). Despite progress in cancer therapy, ovarian cancer mortality has remained virtually unchanged over the past two decades. (Id.) Given the steep survival gradient relative to the stage at which the disease is diagnosed, early detection remains the most important factor in improving long-term survival of ovarian cancer patients.

The poor prognosis of ovarian cancer diagnosed at late stages, the cost and risk associated with confirmatory diagnostic procedures, and its relatively low prevalence in the general population together pose extremely stringent requirements on the sensitivity and specificity of a test for it to be used for screening for ovarian cancer in the general population.

The identification of tumor markers suitable for the early detection and diagnosis of cancer holds great promise to improve the clinical outcome of patients. It is especially important for patients presenting with vague or no symptoms or with tumors that are relatively inaccessible to physical examination. Despite considerable effort directed at early detection, no cost effective screening tests have been developed (Paley, *Curr. Opin. Oncol.*, 13(5):399402 (2001)) and women generally present with disseminated disease at diagnosis. (Ozols et al. Epithelial ovarian cancer. In: Hoskins W J, Perez C A, Young R C, editors. Principles and Practice of Gynecologic Oncology. 3rd ed. Philadelphia: Lippincott, Williams and Wilkins; pages 981-1057 (2000)).

The best-characterized tumor marker, CA125, is negative in approximately 30-40% of stage I ovarian carcinomas and its levels are elevated in a variety of benign diseases. (Meyer et al., *Br. J. Cancer*, 82(9):1535-8 (2000); Buamah, *J. Surg. Oncol.*, 75(4):264-5 (2000); Tuxen et al., *Cancer Treat. Rev.*, 21(3):215-45 (1995)). Its use as a population-based screening tool for early detection and diagnosis of ovarian cancer is hindered by its low sensitivity and specificity (MacDonald et al., *Eur. J. Obstet. Gynecol. Reprod. Biol.*, 82(2):155-7 (1999); Jacobs et al., *Hum. Reprod.*, 4(1):1-12 (1989); Shih et al., Tumor markers in ovarian cancer, Diamandis, Fritsche, Lilja, Chan, and Schwartz, editor; Tumor markers physiology, pathobiology, technology and clinical applications, Philadelphia: AACC Press; in press). Although pelvic and more recently vaginal sonography has been used to screen high-risk patients, neither technique has the sufficient sensitivity and specificity to be applied to the general population (MacDonald et al., supra). Recent efforts in using CA125 in combination with additional tumor markers (Woolas et al., *J. National Cancer Inst.*, 85(21):1748-51 (1993); Woolas et al., *Gynecol. Oncol.*, 59(1):111-6 (1995); Zhang et al., *Gynecol. Oncol.*, 73(1):56-61 (1999); Zhang et al., Use of Multiple Markers to Detect Stage I Epithelial Ovarian Cancers: Neural Network Analysis Improves Performance, American Society of Clinical Oncology (2001); Annual Meeting, Abstract) in a longitudinal risk of cancer model (Skates et al., *Cancer*, 76(10 Supp):2004-10 (1995)), and in tandem with ultrasound as a second line test (Jacobs et al., *Br. Med. J.*, 306(6884):1030-34 (1993); Menon et al., *British Journal of Obstetrics and Gynecology*, 107(2): 165-69 (2000)) have shown promising results in improving overall test specificity, which is critical for a disease such as ovarian cancer that has a relatively low prevalence.

Due to the dismal prognosis of late stage ovarian cancer, it is the general consensus that a physician will accept a test with a minimal positive predictive value of 10%. (Bast et al., *Cancer Treatment and Research*, 107:61-97 (2002)). Extending this to the general population, a general screening test would require a sensitivity greater than 70% and a specificity of 99.6%. Currently, none of the existing serologic markers, such as CA125, CA72-4, or M-CSF, individually delivers such a performance (Bast et al., *Int. J. Biol. Markers*, 13:179-87 (1998)).

Thus, there is a critical need for new serological markers that individually or in combination with other markers or diagnostic modalities deliver the required sensitivity and specificity for early detection of ovarian cancer (Bast et al., Early detection of ovarian cancer: promise and reality, Ovarian Cancer: ISIS Medical Media Ltd., Oxford, UK (2001), in press). Without an acceptable screening test, early detection remains the most critical factor in improving long-term survival of patients with ovarian cancer.

Thus, it is desirable to have a reliable and accurate method of determining the ovarian cancer status in patients, the results of which can then be used to manage subject treatment.

SUMMARY OF THE INVENTION

The present invention fills these needs by providing novel biomarkers and combinations of biomarkers useful for diagnosing ovarian cancer, as well as methods and kits for using the biomarkers to diagnose ovarian cancer.

More specifically, in one aspect, the present invention provides a method for qualifying ovarian cancer status in a subject comprising: (a) measuring at least one biomarker in a biological sample from the subject, wherein the at least one biomarker is selected from the group consisting of the biomarkers of Tables 1, 3 and 4; and (b) correlating the measurement with ovarian cancer status. In one embodiment, the at least one biomarker is selected from the group consisting of ApoC1, Hemoglobin alpha/beta, ApoAII, ApoCII, Calgranulin C, Calgranulin C (truncated form), Calgranulin A, Calcyclin, Transthyretin (doubly charged) and IgG heavy chain. In another embodiment, the method involves measuring each of ApoC1, Hemoglobin alpha/beta, ApoAII, ApoCII, Calgranulin C, Calgranulin C (truncated form), Calgranulin A, Calcyclin, Transthyretin and IgG heavy chain. In another embodiment, the method further comprises measuring some other known biomarker for ovarian cancer, such as CA125.

In another embodiment, the method further comprises measuring some other known biomarker for ovarian cancer, such as CA125. In a further embodiment, the method further comprises measuring and correlating at least one biomarker selected from the group consisting of CA125, transferrin, haptoglobin, ApoA1, transthyretin, ITIH4 internal fragment, beta 2-microglobulin, hepcidin, prostatin, osteopontin, esoinophil-derived neurotoxin, leptin, prolactin, IGF-II, hemoglobin and modified forms thereof. In yet another embodiment, the method further comprises CA125 II, CA15-3, CA19-9, CA72-4, CA 195, tumor associated trypsin inhibitor (TATI), CEA, placental alkaline phosphatase (PLAP), Sialyl TN, galactosyltransferase, macrophage colony stimulating factor (M-CSF, CSF-1), lysophosphatidic acid (LPA), 110 kD component of the subject. extracellular domain of the epidermal growth factor receptor (p110EGFR), tissue kallikreins, e.g., kallikrein 6 and kallikrein 10 (NES-1), prostasin, HE4, creatine kinase B (CKB), LASA, HER-2/neu, urinary gonadotropin peptide, Dianon NB 70/K, Tissue peptide antigen (TPA), SMRP, osteopontin, and haptoglobin, leptin, prolactin, insulin-like growth factor I and insulin-like growth factor II. These additional biomarkers can also be measured and correlated using the other methods, kits and software of the present invention.

In one embodiment of the above method, the at least one biomarker is measured by capturing the biomarker on an adsorbent surface of a SELDI probe and detecting the captured biomarkers by laser desorption-ionization mass spectrometry. In another embodiment, the at least one biomarker is measured by an immunoassay. This latter method is particularly useful when the identity of the biomarker is known. In one embodiment, the sample is ovarian cyst fluid. In a related embodiment, the adsorbent is a member selected from the group consisting of a hydrophobic adsorbent, an anion exchange adsorbent, a cation exchange adsorbent and a metal chelate adsorbent. In yet another embodiment, the adsorbent is a cation exchange adsorbent.

In another embodiment, the biomarkers of the invention are measured by a method other than mass spectrometry or methods that rely on a measurement of the mass of the biomarker. For instance, in certain embodiments, the biomarkers of this invention are measured by immunoassay.

As indicated, the above method is directed to qualifying ovarian cancer status. In one embodiment, the correlating is performed by a software classification algorithm. Generally, in the method of the present invention, the ovarian cancer status is selected from benign ovarian disease, ovarian cancer of low malignant potential, ovarian cancer (malignant) and other malignant conditions. In one embodiment, the ovarian cancer status is selected from benign ovarian disease and ovarian cancer of low malignant potential versus ovarian cancer (malignant) and other malignant conditions. In another embodiment, the ovarian cancer status is selected from ovarian cancer of low malignant potential versus benign ovarian disease, ovarian cancer (malignant) and other malignant conditions. In yet another embodiment, the ovarian cancer status rules out the possibility of benign ovarian disease. In still a further embodiment, the ovarian cancer status rules out the possibility of ovarian cancer (malignant) and other malignant conditions.

In another embodiment, the methods described herein of detecting biomarkers and correlating the measurements with ovarian cancer status further comprise managing subject treatment based on the status. In a related embodiment, if the measurement correlates with ovarian cancer, then managing subject treatment comprises administering a chemotherapeutic agent to the subject. In another embodiment, the methods further comprise measuring the at least one biomarker after subject management and correlating the measurement with disease progression, include determining the rates of disease progression.

The invention also provides a method comprising measuring at least one biomarker in a sample from a subject, wherein the at least one biomarker is selected from the group consisting of biomarkers of Tables 1, 3 and 4.

Another embodiment of the invention provides a method for determining the course of ovarian cancer comprising (a) measuring, at a first time, at least one biomarker in a biological sample from the subject, wherein the at least one biomarker is selected from the group consisting of the biomarkers of Tables 1, 3 and 4; and (b) measuring, at a second time, the at least one biomarker in a biological sample from the subject; and (c) comparing the first measurement and the second measurement; wherein the comparative measurements determine the course of the ovarian cancer.

In yet another embodiment, the at least one biomarker is selected from the group consisting of: ApoC1, Hemoglobin alpha/beta, ApoAII, ApoCII, Calgranulin C, Calgranulin C (truncated form), Calgranulin A and IgG heavy chain. In a further embodiment, the method comprises measuring each of the following biomarkers: ApoC1, Hemoglobin alpha/beta, ApoAII, ApoCII, Calgranulin C, Calgranulin C (truncated form), Calgranulin A and IgG heavy chain. In a related embodiment, the method comprises additionally measuring CA125.

In still another embodiment, the at least one biomarker is selected from the group consisting of: ApoC1, ApoAII, ApoCII, Calgranulin A, Calgranulin C, Calcyclin, and Transthyretin (doubly charged). In another embodiment, the method involves measuring each of ApoC1, ApoAII, ApoCII, Calgranulin A, Calgranulin C, Calcyclin, and Transthyretin (doubly charged). In another embodiment, the method further comprises measuring some other known biomarker for ovarian cancer, such as CA125.

In addition to the methods described herein, the invention also provides compositions comprising a purified biomolecule selected from the biomarkers of Tables 1, 3 and 4. In another embodiment, the invention provides a composition comprising a biospecific capture reagent, e.g., an antibody, that specifically binds a biomolecule selected from the biomarkers of Tables 1, 3 and 4. In a related embodiment, the biospecific capture reagent is bound to a solid support. In yet another embodiment, the invention provides a composition comprising a biospecific capture reagent bound to a biomarker of Tables 1, 3 and 4.

In other embodiments, the invention provides kits. For example, in one embodiment, the invention provides a kit comprising: (a) a solid support comprising at least one capture reagent attached thereto, wherein the capture reagent binds at least one biomarker from a first group consisting of the biomarkers of Tables 1, 3 and 4; and (b) instructions for using the solid support to detect a biomarker of Tables 1, 3 and 4. In a related embodiment, the kit further comprises instructions for using the solid support to detect a biomarker selected from the group consisting of: ApoC1, Hemoglobin alpha/beta, ApoAII, ApoCII, Calgranulin C, Calgranulin C (truncated form), Calgranulin A and IgG heavy chain. In another embodiment, the kit comprises instructions for using the solid support to detect each of the biomarkers: ApoC1, Hemoglobin alpha/beta, ApoAII, ApoCII, Calgranulin C, Calgranulin C (truncated form), Calgranulin A and IgG heavy chain. In yet another embodiment, the kits further comprise instructions for using the solid support to detect CA125.

In still another related embodiment, the kit comprises instructions for using the solid support to detect at least one biomarker is selected from the group consisting of: ApoC1, ApoAII, ApoCII, Calgranulin A, Calgranulin C, Calcyclin, and Transthyretin (doubly charged). In another embodiment, the kit comprises instructions for using the solid support to detect each of ApoC1, ApoAII, ApoCII, Calgranulin A, Calgranulin C, Calcyclin, and Transthyretin (doubly charged). In another embodiment, the kit comprises instructions for using the solid support to detect some other known biomarker for ovarian cancer, such as CA125.

In another related embodiment, the solid support of the kits comprises a capture reagent is a SELDI probe, where the capture reagent is a hydrophobic adsorbent, an anion exchange adsorbent, a cation exchange adsorbent and a metal chelate adsorbent. In yet another embodiment, the kits additionally comprise a container containing at least one of the biomarkers of Tables 1, 3 and 4. In yet another embodiment, the kits additionally comprise a cation exchange chromatography sorbent.

In another embodiment, the invention provides a kit comprising (a) a solid support comprising at least one capture reagent attached thereto, wherein the capture reagents bind at least one biomarker selected from the group consisting of the biomarkers of Tables 1, 3 and 4; and (b) a container containing at least one of the biomarkers. In a related embodiment, the container contains at least one biomarker selected from the group consisting of: ApoC1, Hemoglobin alpha/beta, ApoAII, ApoCII, Calgranulin C, Calgranulin C (truncated form), Calgranulin A and IgG heavy chain. In yet another embodiment, the container contains each of the following biomarkers: ApoC1, Hemoglobin alpha/beta, ApoAII, ApoCII, Calgranulin C, Calgranulin C (truncated form), Calgranulin A and IgG heavy chain. In a related embodiment, the container further contains CA125.

In still another related embodiment, the container contains at least one biomarker selected from the group consisting of: ApoC1, ApoAII, ApoCII, Calgranulin A, Calgranulin C, Calcyclin, and Transthyretin (doubly charged). In another embodiment, the container contains each of ApoC1, ApoAII, ApoCII, Calgranulin A, Calgranulin C, Calcyclin, and Transthyretin (doubly charged). In another embodiment, the container further contains CA125.

In yet another embodiment, the solid support of the kits comprises a capture reagent is a SELDI probe, where the capture reagent is a hydrophobic adsorbent, an anion exchange adsorbent, a cation exchange adsorbent and a metal chelate adsorbent. In yet another embodiment, the kits additionally comprise a container containing at least one of the biomarkers of Tables 1, 3 and 4.

The invention additionally provides a software product comprising code that accesses data attributed to a sample, the data comprising measurement of at least one biomarker in the sample, the biomarker selected from the group consisting of the biomarkers of Tables 1, 3 and 4; and further comprising code that executes a classification algorithm that classifies the ovarian cancer status of the sample as a function of the measurement. In a related embodiment, the software product classifies the ovarian cancer status of the sample as a function of the measurement of a biomarker selected from the group consisting of ApoC1, Hemoglobin alpha/beta, ApoAII, ApoCII, Calgranulin C, Calgranulin C (truncated form), Calgranulin A and IgG heavy chain. In yet another embodiment, the classification algorithm classifies the ovarian cancer status of the sample as a function of the measurement of each of the biomarkers: ApoC1, Hemoglobin alpha/beta, ApoAII, ApoCII, Calgranulin C, Calgranulin C (truncated form), Calgranulin A and IgG heavy chain. In yet another embodiment, the classification algorithm classifies the ovarian cancer status of the sample further as a function of the measurement of CA125.

In a related embodiment, the software product classifies the ovarian cancer status of the sample as a function of the measurement of a biomarker selected from the group consisting of: ApoC1, ApoAII, ApoCII, Calgranulin A, Calgranulin C, Calcyclin, and Transthyretin (doubly charged). In another embodiment, the classification algorithm classifies the ovarian cancer status of the sample as a function of the measurement of each of the biomarkers: ApoC1, ApoAII, ApoCII, Calgranulin A, Calgranulin C, Calcyclin, and Transthyretin (doubly charged). In another embodiment, the classification algorithm classifies the ovarian cancer status of the sample further as a function of the measurement of CA125.

The present invention additionally provides a method which comprises detecting a biomarker of Tables 1, 3 and 4 by mass spectrometry or immunoassay.

In another embodiment, the invention provides a method comprising communicating to a subject a diagnosis relating to ovarian cancer status determined from the correlation of biomarkers in a sample from the subject, wherein the biomarkers are selected from the group consisting of the biomarkers of Tables 1, 3 and 4. In a related embodiment, the diagnosis is communicated to the subject via a computer-generated medium.

In another embodiment, the present invention provides a method for identifying a compound that interacts with a biomarker of Tables 1, 3 and 4, wherein the method comprises (a) contacting a biomarker of Tables 1, 3 and 4 with a test compound; and (b) determining whether the test compound interacts with the biomarker of Tables 1, 3 and 4.

In another embodiment, the invention provides a method for modulating the concentration of Calgranulin C in a cell, wherein the method comprises contacting said cell with an inhibitor, wherein said inhibitor prevents cleavage of Calgranulin C.

The invention additionally provides a method of treating a condition in a subject, wherein said method comprises administering to a subject a therapeutically effective amount of an inhibitor of Calgranulin C, wherein the inhibitor prevents cleavage of Calgranulin C. In a related embodiment, said condition is ovarian cancer.

Other features, objects and advantages of the present invention and its preferred embodiments will become apparent from the detailed description, examples and claims that follow.

BRIEF DESCRIPTION OF THE DRAWINGS

FIG. 1. Representative spectra (A) and corresponding gel views (B) of cyst fluids from individual patients with benign (a, a'), malignant epithelial ovarian cancer (b, b'), and low malignant potential tumors. Fractionated by anion exchange with descending pH (pH 9.0, 7.0, 5.0, 4.0, 3.0), then organic solvent, adsorbed to CM10 ProteinChip arrays, and read at low laser intensity. pH 9.0 elution fractions are shown for each patient. Representative scatter and box plots (C) show variability in "peak intensity" for m/z 10,840 (calgranulin A). The horizontal line in each scatter plot is the mean "peak intensity". Peak m/z 10,840 has significantly greater "peak intensity" in patients with malignant epithelial ovarian cancer.

DETAILED DESCRIPTION OF THE INVENTION AND PREFERRED EMBODIMENTS

I. Introduction

A biomarker is an organic biomolecule which is differentially present in a sample taken from a subject of one phenotypic status (e.g., having a disease) as compared with another phenotypic status (e.g., not having the disease). A biomarker is differentially present between different phenotypic statuses if the mean or median expression level of the biomarker in the different groups is calculated to be statistically significant: Common tests for statistical significance include, among others, t-test, ANOVA, Kruskal-Wallis, Wilcoxon, Mann-Whitney and odds ratio. Biomarkers, alone or in combination, provide measures of relative risk that a subject belongs to one phenotypic status or another. Therefore, they are useful as markers for disease (diagnostics), therapeutic effectiveness of a drug (theranostics) and drug toxicity.

II. Biomarkers for Ovarian Cancer

This invention provides polypeptide-based biomarkers that are differentially present in subjects having ovarian cancer, in particular, ovarian cancer (malignant, such as invasive epithelial ovarian cancer), ovarian cancer of low malignant potential ((LMP), borderline disease), benign ovarian disease and other malignant conditions (such as malignancies other than invasive epithelial ovarian cancer, including metastatic cancer (e.g., gastric cancer metastasized to the ovary), mesothelioma, a stromal ovarian cancer, etc.)). The biomarkers are characterized by mass-to-charge ratio as determined by mass spectrometry, by the shape of their spectral peak in time-of-flight mass spectrometry and by their binding characteristics to adsorbent surfaces. These characteristics provide one method to determine whether a particular detected biomolecule is a biomarker of this invention. These characteristics represent inherent characteristics of the biomolecules and not process limitations in the manner in which the biomolecules are discriminated. In one aspect, this invention provides these biomarkers in isolated form.

The biomarkers were discovered using SELDI technology employing ProteinChip arrays from Ciphergen Biosystems, Inc. (Fremont, Calif.) ("Ciphergen"). Ovarian cyst fluid was collected from subjects diagnosed with ovarian cancer (invasive epithelial ovarian cancer), ovarian cancer of low malignant potential (borderline disease), other malignant conditions and benign ovarian disease. A portion of the samples were left unfactionated and the other portion of samples were fractionated by anion exchange chromatography. Unfractionated and fractionated samples were applied to SELDI biochips and spectra of polypeptides in the samples were generated by time-of-flight mass spectrometry on a Ciphergen PBSII mass spectrometer. The spectra thus obtained were analyzed by Ciphergen Express™ Data Manager Software with Biomarker Wizard and Biomarker Pattern Software from Ciphergen Biosystems, Inc. The mass spectra for each group were subjected to scatter plot analysis. A Mann-Whitney test analysis was employed to compare ovarian cancer and control groups for each protein cluster in the scatter plot, and proteins were selected that differed significantly ($p<0.0001$) between the two groups. This method is described in more detail in the Example Section.

The biomarkers thus discovered are presented in Table 1. The "ProteinChip assay" column refers to chromatographic fraction, if applicable) in which the biomarker is found, the type of biochip to which the biomarker binds and whether the biomarker is up- or down-regulated in ovarian cancer, as per the Example Section.

TABLE 1

| Marker ID, m/z | P-Value | Up or down regulated in ovarian cancer | ProteinChip ® assay |
|---|---|---|---|
| M6420/6640 ApoCI | <0.001 | Up in Malignancy[2] | Unfractionated, H50, Q10 Fraction 1, CM10 |
| M7570/7930 Hemoglobin Alpha/Beta[1] | <0.001 | Up in Malignancy | Unfractionated, Q10 |
| M8690/8810 ApoAII | <0.001 | Down in LMP[3] | Unfractionated, H50, Q10 |
| M8920 ApoCII | <0.001 | Down in LMP | Unfractionated, H50 |
| M10210 Calcyclin | <0.001 | r/o Benign[4] | Unfractionated, H50, Q10 |
| M10430 Calgranulin C | <0.001 | r/o Benign | Unfractionated, H50, Q10 |
| M54000 IgG heavy chain | <0.001 | r/o Malignancy[4] | Unfractionated, IMAC, H50 Fraction 4, IMAC30 |
| M10840 Calgranulin A | <0.001 | r/o Benign | Fraction 1, CM10, IMAC30 |
| M32600 | <0.001 | Down in Malignancy[6] | Fraction 1, CM10 |
| M51000 | <0.001 | Down in Malignancy | Fraction 3, CM10, IMAC30 |
| M6880 Transthyretin (doubly charged) | <0.001 | Up in Malignancy | Fraction 4, CM10 |
| M8660 ApoII | <0.001 | Down in LMP | Fraction 4, CM10 |
| M75000 | <0.001 | Up in Malignancy | Fraction 4, CM10 |
| M83820 | <0.001 | Up in Malignancy | Fraction 4, CM10 |
| M94500 | <0.001 | Up in Malignancy | Fraction 4, CM10 |
| M146000 | <0.001 | Up in Malignancy | Fraction 4, CM10 |
| M4249 | <0.001 | Up in Malignancy | Fraction 5, CM10 |
| M4562 | <0.001 | Up in Malignancy | Fraction 5, CM10 |

TABLE 1-continued

| Marker ID, m/z | P-Value | Up or down regulated in ovarian cancer | ProteinChip ® assay |
| --- | --- | --- | --- |
| M4630 | <0.001 | Up in Malignancy | Fractions 4, 5, IMAC30, CM10 |
| M6936 | <0.001 | Up in Malignancy | Fraction 5, CM10 |
| M63000 | <0.001 | Down in Malignancy | Fraction 6, CM10 |

[1]It is noted that the hemoglobin alpha and hemoglobin beta are doubly charged in the SELDI detection assay set forth in the Example Section
[2]"Up in Malignancy" means that the biomarker is up-regulated in ovarian cancer and other malignant conditions (such as malignancies other than invasive epithelial ovarian cancer, including metastatic cancer (e.g., gastric cancer frequently metastasizes to the ovary), mesothelioma, a stromal ovarian cancer, etc.) versus benign ovarian disease and ovarian cancer of low malignant potential (LMP) (borderline disease).
[3]"Down in LMP" means that the biomarker is down-regulated in ovarian cancer of low malignant potential versus the other three groups (i.e., benign ovarian disease, ovarian cancer (malignant) and other malignant conditions).
[4]"r/o benign" means that the presence of the biomarker rules out the possibility of benign disease, but it is not adequate, alone, to made a diagnosis among the other three groups (ovarian cancer LMP, ovarian cancer (malignant) and other malignant conditions).
[5]"r/o Malignant" means that the presence of the biomarker rules out the possibility of malignant disease, but is not adequate on its own to make a diagnosis of benign ovarian disease.
[6]"Down in Malignancy" means that the biomarker is up-regulated in ovarian cancer and other malignant conditions versus benign ovarian disease and ovarian cancer of low malignant potential (LMP) (borderline disease).

The biomarkers of this invention are characterized by their mass-to-charge ratio as determined by mass spectrometry. The mass-to-charge ratio of each biomarker is provided in Table 1, above, Tables 2 and 3, below, after the "M." Thus, for example, M6420 has a measured mass-to-charge ratio of 6420. The mass-to-charge ratios were determined from mass spectra generated on a Ciphergen Biosystems, Inc. PBS II mass spectrometer. This instrument has a mass accuracy of about +/−0.15 percent. Additionally, the instrument has a mass resolution of about 400 to 1000 m/dm, where m is mass and dm is the mass spectral peak width at 0.5 peak height. The mass-to-charge ratio of the biomarkers was determined using Biomarker Wizard™ software (Ciphergen Biosystems, Inc.). Biomarker Wizard assigns a mass-to-charge ratio to a biomarker by clustering the mass-to-charge ratios of the same peaks from all the spectra analyzed, as determined by the PBSII, taking the maximum and minimum mass-to-charge-ratio in the cluster, and dividing by two. Accordingly, the masses provided reflect these specifications.

The biomarkers of this invention are further characterized by the shape of their spectral peak in time-of-flight mass spectrometry.

The biomarkers of this invention are further characterized by their binding properties on chromatographic surfaces. Examples of chromatographic surfaces that the biomarkers of this invention bind include, but are not limited to, a hydrophobic adsorbent (such as the Ciphergen® H50 ProteinChip® array), an anion exchange adsorbent (such as the Ciphergen® Q10 ProteinChip® array), a cation exchange adsorbent (such as the Ciphergen® CM10 ProteinChip® array) and a metal chelate adsorbent (such as the Ciphergen® IMAC-30 ProteinChip® array). A number of the biomarkers bind to a hydrophobic adsorbent (such as the Ciphergen® H50 ProteinChip® array) using a binding and washing buffer of 10% acetonitrile. Some of the biomarkers bind to an anion exchange adsorbent (such as the Ciphergen® Q10 ProteinChip® array) using a binding and washing buffer of 50 mM Tris buffer at pH 8.0. A number of the biomarkers bind to a metal chelate adsorbent (such as the Ciphergen® IMAC-30 ProteinChip® array coupled with copper) using, for example, a binding and washing buffer of 50 mM Tris pH 8.0/500 mM NaCl. Most of the biomarkers bind to cation exchange adsorbents (e.g., the Ciphergen CM10 ProteinChip® array) after washing with 100 mM sodium acetate at pH 4.

The identity of certain of the biomarkers of this invention has been determined and is indicated in Table 1. The method by which this determination was made is described in the Example Section. For biomarkers whose identify has been determined, the presence of the biomarker can be determined by other methods known in the art (e.g., by immunoassay).

Because the biomarkers of this invention are characterized by mass-to-charge ratio, binding properties and spectral shape, they can be detected by mass spectrometry without knowing their specific identity. However, if desired, biomarkers whose identity is not determined can be identified by, for example, determining the amino acid sequence of the polypeptides. For example, a biomarker can be peptide-mapped with a number of enzymes, such as trypsin or V8 protease, and the molecular weights of the digestion fragments can be used to search databases for sequences that match the molecular weights of the digestion fragments generated by the various enzymes. Alternatively, protein biomarkers can be sequenced using tandem MS technology. In this method, the protein is isolated by, for example, gel electrophoresis. A band containing the biomarker is cut out and the protein is subject to protease digestion. Individual protein fragments are separated by a first mass spectrometer. The fragment is then subjected to collision-induced cooling, which fragments the peptide and produces a polypeptide ladder. A polypeptide ladder is then analyzed by the second mass spectrometer of the tandem MS. The difference in masses of the members of the polypeptide ladder identifies the amino acids in the sequence. An entire protein can be sequenced this way, or a sequence fragment can be subjected to database mining to find identity candidates.

The preferred biological source for detection of the biomarkers is ovarian cyst fluid. However, in other embodiments, the biomarkers are detected in other bodily fluids, e.g., serum, blood or urine.

The biomarkers of this invention are biomolecules. Accordingly, this invention provides these biomolecules in isolated form. The biomarkers can be isolated from biological fluids, such as urine or serum. They can be isolated by any method known in the art, based on both their mass and their binding characteristics. For example, a sample comprising the biomolecules can be subject to chromatographic fractionation, as described herein, and subject to further separation by, e.g., acrylamide gel electrophoresis. Knowledge of the identity of the biomarker also allows their isolation by immunoaffinity chromatography.

III. Biomarkers and Different Forms of a Protein

Proteins frequently exist in a sample in a plurality of different forms characterized by a detectably different mass. These forms can result from either or both of pre- and post-translational modification. Pre-translational modified forms include allelic variants, slice variants and RNA editing forms. Post-translationally modified forms include forms resulting from proteolytic cleavage (e.g., fragments of a parent protein), glycosylation, phosphorylation, lipidation, oxidation, methylation, cystinylation, sulphonation and acetylation. When detecting or measuring a protein in a sample, the ability to differentiate between different forms of a protein depends upon the nature of the difference and the method used to detect or measure. For example, an immunoassay using a monoclonal antibody will detect all forms of a protein containing the eptiope and will not distinguish between them. However, a sandwich immunoassay that uses two antibodies directed against different epitopes on a protein will detect all forms of the protein that contain both epitopes and will not detect those forms that contain only one of the epitopes. In diagnostic assays, the inability to distinguish different forms of a protein has little impact when the forms detected by the particular method used are equally good biomarkers as any particular form. However, when a particular form (or a subset of particular forms) of a protein is a better biomarker than the collection of different forms detected together by a particular method, the power of the assay may suffer. In this case, it is useful to employ an assay method that distinguishes between forms of a protein and that specifically detects and measures a desired form or forms of the protein. Distinguishing different forms of an analyte or specifically detecting a particular form of an analyte is referred to as "resolving" the analyte.

Mass spectrometry is a particularly powerful methodology to resolve different forms of a protein because the different forms typically have different masses that can be resolved by mass spectrometry. Accordingly, if one form of a protein is a superior biomarker for a disease than another form of the biomarker, mass spectrometry may be able to specifically detect and measure the useful form where traditional immunoassay fails to distinguish the forms and fails to specifically detect to useful biomarker.

One useful methodology combines mass spectrometry with immunoassay. First, a biospecific capture reagent (e.g., an antibody, aptamer or Affibody that recognizes the biomarker and other forms of it) is used to capture the biomarker of interest. Preferably, the biospecific capture reagent is bound to a solid phase, such as a bead, a plate, a membrane or an array. After unbound materials are washed away, the captured analytes are detected and/or measured by mass spectrometry. (This method also will also result in the capture of protein interactors that are bound to the proteins or that are otherwise recognized by antibodies and that, themselves, can be biomarkers.) Various forms of mass spectrometry are useful for detecting the protein forms, including laser desorption approaches, such as traditional MALDI or SELDI, and electrospray ionization.

Thus, when reference is made herein to detecting a particular protein or to measuring the amount of a particular protein, it means detecting and measuring the protein with or without resolving various forms of protein. For example, the step of "measuring Calgranulin C" includes measuring any and/or all forms of Calgranulin C by means that do not differentiate between various forms of the protein in a sample (e.g., certain immunoassays) as well as by means that differentiate some forms from other forms or that measure a specific form of the protein (e.g., mass spectrometry). In contrast, when it is desired to measure a particular form or forms of a protein (e.g., a particular form of Calgranulin C including forms modified by truncation, phosphorylation, glycosylation, etc.), the particular form (or forms) is specified. For example, "measuring M10430" means measuring a polypeptide having an apparent molecular weight of 10430 Da that, therefore, distinguishes M10430 from other forms of Calgranulin C.

IV. Detection of Biomarkers for Ovarian Cancer

The biomarkers of this invention can be detected by any suitable method. Detection paradigms that can be employed to this end include optical methods, electrochemical methods (voltametry and amperometry techniques), atomic force microscopy, and radio frequency methods, e.g., multipolar resonance spectroscopy. Illustrative of optical methods, in addition to microscopy, both confocal and non-confocal, are detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

In one embodiment, a sample is analyzed by means of a biochip. Biochips generally comprise solid substrates and have a generally planar surface, to which a capture reagent (also called an adsorbent or affinity reagent) is attached. Frequently, the surface of a biochip comprises a plurality of addressable locations, each of which has the capture reagent bound there.

Protein biochips are biochips adapted for the capture of polypeptides. Many protein biochips are described in the art. These include, for example, protein biochips produced by Ciphergen Biosystems, Inc. (Fremont, Calif.), Zyomyx (Hayward, Calif.), Invitrogen (Carlsbad, Calif.), Biacore (Uppsala, Sweden) and Procognia (Berkshire, UK). Examples of such protein biochips are described in the following patents or published patent applications: U.S. Pat. No. 6,225,047 (Hutchens et al.); U.S. Pat. No. 6,537,749 (Kuimelis et al.); U.S. Pat. No. 6,329,209 (Wagner et al.); PCT International Publication No. WO 00/56934 (Englert et al.); PCT International Publication No. WO 03/048768 (Boutell et al.) and U.S. Pat. No. 5,242,828 (Bergstrom et al.).

Detection by Mass Spectrometry

In a preferred embodiment, the biomarkers of this invention are detected by mass spectrometry, a method that employs a mass spectrometer to detect gas phase ions. Examples of mass spectrometers are time-of-flight, magnetic sector, quadrupole filter, ion trap, ion cyclotron resonance, electrostatic sector analyzer and hybrids of these.

In a further preferred method, the mass spectrometer is a laser desorption/ionization mass spectrometer. In laser desorption/ionization mass spectrometry, the analytes are placed on the surface of a mass spectrometry probe, a device adapted to engage a probe interface of the mass spectrometer and to present an analyte to ionizing energy for ionization and introduction into a mass spectrometer. A laser desorption mass spectrometer employs laser energy, typically from an ultraviolet laser, but also from an infrared laser, to desorb analytes from a surface, to volatilize and ionize them and make them available to the ion optics of the mass spectrometer. The analysis of proteins by LDI can take the form of MALDI or of SELDI.

Laser desorption/ionization in a single TOF instrument typically is performed in linear extraction mode. Tandem mass spectrometers can employ orthogonal extraction modes.

SELDI

A preferred mass spectrometric technique for use in the invention is "Surface Enhanced Laser Desorption and Ionization" or "SELDI," as described, for example, in U.S. Pat. Nos. 5,719,060 and 6,225,047, both to Hutchens et al. This refers to a method of desorption/ionization gas phase ion spectrometry (e.g., mass spectrometry) in which an analyte (here, one or more of the biomarkers) is captured on the surface of a SELDI mass spectrometry probe. There are several versions of SELDI.

One version of SELDI is called "affinity capture mass spectrometry." It also is called "Surface-Enhanced Affinity Capture" or "SEAC." This version involves the use of probes that have a material on the probe surface that captures analytes through a non-covalent affinity interaction (adsorption) between the material and the analyte. The material is variously called an "adsorbent," a "capture reagent," an "affinity reagent" or a "binding moiety." Such probes can be referred to as "affinity capture probes" and as having an "adsorbent surface." The capture reagent can be any material capable of binding an analyte. The capture reagent is attached to the probe surface by physisorption or chemisorption. In certain embodiments the probes have the capture reagent already attached to the surface. In other embodiments, the probes are pre-activated and include a reactive moiety that is capable of binding the capture reagent, e.g., through a reaction forming a covalent or coordinate covalent bond. Epoxide and acyl-imidizole are useful reactive moieties to covalently bind polypeptide capture reagents such as antibodies or cellular receptors. Nitrilotriacetic acid and iminodiacetic acid are useful reactive moieties that function as chelating agents to bind metal ions that interact non-covalently with histidine containing peptides. Adsorbents are generally classified as chromatographic adsorbents and biospecific adsorbents.

"Chromatographic adsorbent" refers to an adsorbent material typically used in chromatography. Chromatographic adsorbents include, for example, ion exchange materials, metal chelators (e.g., nitrilotriacetic acid or iminodiacetic acid), immobilized metal chelates, hydrophobic interaction adsorbents, hydrophilic interaction adsorbents, dyes, simple biomolecules (e.g., nucleotides, amino acids, simple sugars and fatty acids) and mixed mode adsorbents (e.g., hydrophobic attraction/electrostatic repulsion adsorbents).

"Biospecific adsorbent" refers to an adsorbent comprising a biomolecule, e.g., a nucleic acid molecule (e.g., an aptamer), a polypeptide, a polysaccharide, a lipid, a steroid or a conjugate of these (e.g., a glycoprotein, a lipoprotein, a glycolipid, a nucleic acid (e.g., DNA)-protein conjugate). In certain instances, the biospecific adsorbent can be a macromolecular structure such as a multiprotein complex, a biological membrane or a virus. Examples of biospecific adsorbents are antibodies, receptor proteins and nucleic acids. Biospecific adsorbents typically have higher specificity for a target analyte than chromatographic adsorbents. Further examples of adsorbents for use in SELDI can be found in U.S. Pat. No. 6,225,047. A "bioselective adsorbent" refers to an adsorbent that binds to an analyte with an affinity of at least $10^{-8}$ M.

Protein biochips produced by Ciphergen Biosystems, Inc. comprise surfaces having chromatographic or biospecific adsorbents attached thereto at addressable locations. Ciphergen's ProteinChip® arrays include NP20 (hydrophilic); 114 and H50 (hydrophobic); SAX-2, Q-10 and LSAX-30 (anion exchange); WCX-2, CM-10 and LWCX-30 (cation exchange); IMAC-3, IMAC-30 and IMAC-50 (metal chelate); and PS-10, PS-20 (reactive surface with acyl-imidizole, epoxide) and PG-20 (protein G coupled through acyl-imidizole). Hydrophobic ProteinChip arrays have isopropyl or nonylphenoxy-poly(ethylene glycol)methacrylate functionalities. Anion exchange ProteinChip arrays have quaternary ammonium functionalities. Cation exchange ProteinChip arrays have carboxylate functionalities. Immobilized metal chelate ProteinChip arrays have nitrilotriacetic acid functionalities (IMAC-3 and IMAC-30) or O-methacryloyl-N,N-bis-carboxymethyl tyrosine functionalities (IMAC-50) that adsorb transition metal ions, such as copper, nickel, zinc, and gallium, by chelation. Preactivated ProteinChip arrays have acyl-imidizole or epoxide functional groups that can react with groups on proteins for covalent binding.

Such biochips are further described in: U.S. Pat. No. 6,579,719 (Hutchens et al., "Retentate Chromatography," Jun. 17, 2003); U.S. Pat. No. 6,897,072 (Rich et al. "Probes for a Gas Phase Ion Spectrometer," May 24, 2005); U.S. Pat. No. 6,555,813 (Beecher et al., "Sample Holder with Hydrophobic Coating for Gas Phase Mass Spectrometer," Apr. 29, 2003); U.S. Patent Publication No. U.S. 2003 0032043 A1 (Pohl et al. "Latex Based Adsorbent Chip," Jul. 16, 2002); PCT International Publication No. WO 03/040700 (Urn et al., "Hydrophobic Surface Chip," May 15, 2003); U.S. Patent Publication No. US 2003/0218130 A1 (Boschetti et al., "Biochips With Surfaces Coated With Polysaccharide-Based Hydrogels," Apr. 14, 2003) and U.S. Pat. No. 7,045,366 (Huang et al., "Photocrosslinked Hydrogel Surface Coatings," May 16, 2006.

In general, a probe with an adsorbent surface is contacted with the sample for a period of time sufficient to allow the biomarker or biomarkers that may be present in the sample to bind to the adsorbent. After an incubation period, the substrate is washed to remove unbound material. Any suitable washing solutions can be used; preferably, aqueous solutions are employed. The extent to which molecules remain bound can be manipulated by adjusting the stringency of the wash. The elution characteristics of a wash solution can depend, for example, on pH, ionic strength, hydrophobicity, degree of chaotropism, detergent strength, and temperature. Unless the probe has both SEAC and SEND properties (as described herein), an energy absorbing molecule then is applied to the substrate with the bound biomarkers.

In yet another method, one can capture the biomarkers with a solid-phase bound immuno-adsorbent that has antibodies that bind the biomarkers. After washing the adsorbent to remove unbound material, the biomarkers are eluted from the solid phase, applied to a SELDI biochip that binds the biomarkers and analyzed by SELDI.

The biomarkers bound to the substrates are detected in a gas phase ion spectrometer such as a time-of-flight mass spectrometer. The biomarkers are ionized by an ionization source such as a laser, the generated ions are collected by an ion optic assembly, and then a mass analyzer disperses and analyzes the passing ions. The detector then translates information of the detected ions into mass-to-charge ratios. Detection of a biomarker typically will involve detection of signal intensity. Thus, both the quantity and mass of the biomarker can be determined.

SEND

Another method of laser desorption mass spectrometry is called Surface-Enhanced Neat Desorption ("SEND"). SEND involves the use of probes comprising energy absorbing molecules that are chemically bound to the probe surface ("SEND probe"). The phrase "energy absorbing molecules" (EAM)

denotes molecules that are capable of absorbing energy from a laser desorption/ionization source and, thereafter, contribute to desorption and ionization of analyte molecules in contact therewith. The EAM category includes molecules used in MALDI, frequently referred to as "matrix," and is exemplified by cinnamic acid derivatives, sinapinic acid (SPA), cyano-hydroxy-cinnamic acid (CHCA) and dihydroxybenzoic acid, ferulic acid, and hydroxyaceto-phenone derivatives. In certain embodiments, the energy absorbing molecule is incorporated into a linear or cross-linked polymer, e.g., a polymethacrylate. For example, the composition can be a co-polymer of α-cyano-4-methacryloyloxycinnamic acid and acrylate. In another embodiment, the composition is a co-polymer of α-cyano-4-methacryloyloxycinnamic acid, acrylate and 3-(triethoxy)silyl propyl methacrylate. In another embodiment, the composition is a co-polymer of α-cyano-4-methacryloyloxycinnamic acid and octadecylmethacrylate ("C18 SEND"). SEND is further described in U.S. Pat. No. 6,124,137 and PCT International Publication No. WO 03/64594 (Kitagawa, "Monomers And Polymers Having Energy Absorbing Moieties of Use In Desorption/Ionization Of Analytes," Aug. 7, 2003).

SEAC/SEND is a version of SELDI in which both a capture reagent and an energy absorbing molecule are attached to the sample presenting surface. SEAC/SEND probes therefore allow the capture of analytes through affinity capture and ionization/desorption without the need to apply external matrix. The C18 SEND biochip is a version of SEAC/SEND, comprising a C18 moiety which functions as a capture reagent, and a CHCA moiety which functions as an energy absorbing moiety.

SEPAR

Another version of LDI is called Surface-Enhanced Photolabile Attachment and Release ("SEPAR"). SEPAR involves the use of probes having moieties attached to the surface that can covalently bind an analyte, and then release the analyte through breaking a photolabile bond in the moiety after exposure to light, e.g., to laser light (see, U.S. Pat. No. 5,719,060). SEPAR and other forms of SELDI are readily adapted to detecting a biomarker or biomarker profile, pursuant to the present invention.

MALDI

MALDI is a traditional method of laser desorption/ionization used to analyte biomolecules such as proteins and nucleic acids. In one MALDI method, the sample is mixed with matrix and deposited directly on a MALDI array. However, the complexity of biological samples such as serum and urine makes this method less than optimal without prior fractionation of the sample. Accordingly, in certain embodiments with biomarkers are preferably first captured with biospecific (e.g., an antibody) or chromatographic materials coupled to a solid support such as a resin (e.g., in a spin column). Specific affinity materials that bind the biomarkers of this invention are described above. After purification on the affinity material, the biomarkers are eluted and then detected by MALDI.

In another mass spectrometry method, the biomarkers are first captured on a chromatographic resin having chromatographic properties that bind the biomarkers. In the present example, this could include a variety of methods. For example, one could capture the biomarkers on a cation exchange resin, such as CM Ceramic HyperD F resin, wash the resin, elute the biomarkers and detect by MALDI. Alternatively, this method could be preceded by fractionating the sample on an anion exchange resin before application to the cation exchange resin. In another alternative, one could fractionate on an anion exchange resin and detect by MALDI directly. In yet another method, one could capture the biomarkers on an immuno-chromatographic resin that comprises antibodies that bind the biomarkers, wash the resin to remove unbound material, elute the biomarkers from the resin and detect the eluted biomarkers by MALDI or by SELDI.

Other Forms of Ionization in Mass Spectrometry

In another method, the biomarkers are detected by LC-MS or LC-LC-MS. This involves resolving the proteins in a sample by one or two passes through liquid chromatography, followed by mass spectrometry analysis, typically electrospray ionization.

Data Analysis

Analysis of analytes by time-of-flight mass spectrometry generates a time-of-flight spectrum. The time-of-flight spectrum ultimately analyzed typically does not represent the signal from a single pulse of ionizing energy against a sample, but rather the sum of signals from a number of pulses. This reduces noise and increases dynamic range. This time-of-flight data is then subject to data processing. In Ciphergen's ProteinChip® software, data processing typically includes TOF-to-M/Z transformation to generate a mass spectrum, baseline subtraction to eliminate instrument offsets and high frequency noise filtering to reduce high frequency noise.

Data generated by desorption and detection of biomarkers can be analyzed with the use of a programmable digital computer. The computer program analyzes the data to indicate the number of biomarkers detected, and optionally the strength of the signal and the determined molecular mass for each biomarker detected. Data analysis can include steps of determining signal strength of a biomarker and removing data deviating from a predetermined statistical distribution. For example, the observed peaks can be normalized, by calculating the height of each peak relative to some reference.

The computer can transform the resulting data into various formats for display. The standard spectrum can be displayed, but in one useful format only the peak height and mass information are retained from the spectrum view, yielding a cleaner image and enabling biomarkers with nearly identical molecular weights to be more easily seen. In another useful format, two or more spectra are compared, conveniently highlighting unique biomarkers and biomarkers that are up- or down-regulated between samples. Using any of these formats, one can readily determine whether a particular biomarker is present in a sample.

Analysis generally involves the identification of peaks in the spectrum that represent signal from an analyte. Peak selection can be done visually, but software is available, as part of Ciphergen's ProteinChip® software package, that can automate the detection of peaks. In general, this software functions by identifying signals having a signal-to-noise ratio above a selected threshold and labeling the mass of the peak at the centroid of the peak signal. In one useful application, many spectra are compared to identify identical peaks present in some selected percentage of the mass spectra. One version of this software clusters all peaks appearing in the various spectra within a defined mass range, and assigns a mass (M/Z) to all the peaks that are near the mid-point of the mass (M/Z) cluster.

Software used to analyze the data can include code that applies an algorithm to the analysis of the signal to determine whether the signal represents a peak in a signal that corresponds to a biomarker according to the present invention. The software also can subject the data regarding observed biomarker peaks to classification tree or ANN analysis, to determine whether a biomarker peak or combination of biomarker peaks is present that indicates the status of the particular clinical parameter under examination. Analysis of the data may be "keyed" to a variety of parameters that are obtained, either directly or indirectly, from the mass spectrometric analysis of the sample. These parameters include, but are not limited to, the presence or absence of one or more peaks, the shape of a peak or group of peaks, the height of one or more peaks, the log of the height of one or more peaks, and other arithmetic manipulations of peak height data.

General Protocol for SELDI Detection of Biomarkers for Ovarian Cancer

A preferred protocol for the detection of the biomarkers of this invention is as follows. In another embodiment, the biological sample to be tested, e.g., ovarian cyst fluid, preferably is subject to pre-fractionation before SELDI analysis. The prefractionation step often simplifies the sample and improves sensitivity. A preferred method of pre-fractionation involves contacting the sample with an anion exchange chromatographic material, such as Q HyperD (BioSepra, SA). The bound materials are then subject to stepwise pH elution using buffers at pH 9, pH 7, pH 5 and pH 4. (The fractions in which the biomarkers are eluted also are indicated in Table 1). Various fractions containing the biomarker are collected. In another embodiment, the biological sample to be tested, e.g., ovarian cyst fluid samples, is not subject to a pre-fractionation step, but is used in the chip binding step unfractionated.

The sample to be tested (either unfractionated or pre-fractionated) is then contacted with an affinity capture probe. Examples of affinity capture probes of chromatographic surfaces that the biomarkers of this invention bind include, but are not limited to, a hydrophobic adsorbent (such as the Ciphergen® H50 ProteinChip® array), an anion exchange adsorbent (such as the Ciphergen® Q10 ProteinChip® array), a cation exchange adsorbent (such as the Ciphergen® CM10 ProteinChip® array) and a metal chelate adsorbent (such as the Ciphergen® IMAC-30 ProteinChip® array). The probe is washed with a buffer that will retain the biomarker while washing away unbound molecules. A suitable wash for each biomarker is the buffer identified in the Example Section. The biomarkers are detected by laser desorption/ionization mass spectrometry.

Alternatively, samples may be diluted, with or without denaturing, in the appropriate array binding buffer and bound and washed under conditions optimized for detecting each analyte.

Alternatively, if antibodies that recognize the biomarker are available, for example in the case of Apolipoprotein C1 (ApoC1), hemoglobin alpha, hemoglobin beta, Apolipoprotein AII (ApoAII), Apolipoprotein CII (ApoCII), Calgranulin C (both full-length and truncated form), Calgranulin A, IgG heavy chain, Calcyclin and Transthyretin, these can be attached to the surface of a probe, such as a pre-activated PS10 or PS20 ProteinChip array (Ciphergen Biosystems, Inc.). These antibodies can capture the biomarkers from a sample onto the probe surface. Then the biomarkers can be detected by, e.g., laser desorption/ionization mass spectrometry.

Any robot that performs fluidics operations can be used in these assays, for example, those available from Hewlett Packard and Hamilton.

Detection by Immunoassay

In another embodiment of the invention, the biomarkers of the invention are measured by a method other than mass spectrometry or methods that rely on a measurement of the mass of the biomarker. In another embodiment, the biomarkers of this invention are measured by immunoassay. Immunoassay requires biospecific capture reagents, such as antibodies, to capture the biomarkers. Antibodies can be produced by methods well known in the art, e.g., by immunizing animals with the biomarkers. Biomarkers can be isolated from samples based on their binding characteristics. Alternatively, if the amino acid sequence of a polypeptide biomarker is known, the polypeptide can be synthesized and used to generate antibodies by methods well known in the art.

This invention contemplates traditional immunoassays including, for example, sandwich immunoassays including ELISA or fluorescence-based immunoassays, as well as other enzyme immunoassays. Nephelometry is an assay done in liquid phase, in which antibodies are in solution. Binding of the antigen to the antibody results in changes in absorbance, which is measured. In the SELDI-based immunoassay, a biospecific capture reagent for the biomarker is attached to the surface of an MS probe, such as a pre-activated ProteinChip array. The biomarker is then specifically captured on the biochip through this reagent, and the captured biomarker is detected by mass spectrometry.

V. Determination of Subject Ovarian Cancer Status

The biomarkers of the invention can be used in diagnostic tests to assess ovarian cancer status in a subject, e.g., to diagnose ovarian cancer. The phrase "ovarian cancer status" includes any distinguishable manifestation of the disease. For example, ovarian cancer disease status includes, without limitation, the presence or absence of disease (e.g., ovarian cancer (malignant) versus ovarian cancer of low malignant potential versus benign ovarian disease versus other malignant conditions), the risk of developing disease, the stage of the disease, the progress of disease (e.g., progress of disease or remission of disease over time) and the effectiveness or response to treatment of disease. Based on this status, further procedures may be indicated, including additional diagnostic tests or therapeutic procedures or regimens.

The correlation of test results with ovarian cancer status applying a classification algorithm of some kind to the results to generate the status. The classification algorithm may be as simple as determining whether or not the amount of a given biomarker measured is above or below a particular cut-off number. When multiple biomarkers are used, the classification algorithm may be a linear regression formula. Alternatively, the classification algorithm may be the product of any of a number of learning algorithms described herein.

In the case of complex classification algorithms, it may be necessary to perform the algorithm on the data, thereby determining the classification, using a computer, e.g., a programmable digital computer. In either case, one can then record the status on tangible medium, for example, in computer-readable format such as a memory drive or disk or simply printed on paper. The result also could be reported on a computer screen.

Single Markers

The power of a diagnostic test to correctly predict status is commonly measured as the sensitivity of the assay, the specificity of the assay or the area under a receiver operated characteristic ("ROC") curve. Sensitivity is the percentage of true positives that are predicted by a test to be positive, while specificity is the percentage of true negatives that are predicted by a test to be negative. An ROC curve provides the sensitivity of a test as a function of 1-specificity. The greater the area under the ROC curve, the more powerful the predictive value of the test. Other useful measures of the utility of a test are positive predictive value and negative predictive value. Positive predictive value is the percentage of people who test positive that are actually positive. Negative predictive value is the percentage of people who test negative that are actually negative.

The biomarkers of this invention show a statistical difference in different ovarian cancer statuses of at least $p \leq 0.05$, $p \leq 10^{-2}$, $p \leq 10^{-3}$, $p \leq 10^{-4}$ or $p \leq 10^{-5}$. Diagnostic tests that use these biomarkers alone or in combination show a sensitivity and specificity of at least 75%, at least 80%, at least 85%, at least 90%, at least 95%, at least 98% and about 100%.

Each biomarker listed in Tables 1, 3 and 4 is differentially present in ovarian cancer (malignant), in ovarian cancer LMP, in benign ovarian disease or in other malignant conditions), and, therefore, each is individually useful in aiding in the determination of ovarian cancer status. The method involves, first, measuring the selected biomarker in a subject sample using the methods described herein, e.g., capture on a SELDI biochip followed by detection by mass spectrometry and, second, comparing the measurement with a diagnostic amount or cut-off that distinguishes a positive ovarian cancer status from a negative ovarian cancer status. The diagnostic amount represents a measured amount of a biomarker above which or below which a subject is classified as having a particular ovarian cancer status. For example, if the biomarker is up-regulated compared to normal during ovarian cancer, then a measured amount above the diagnostic cutoff provides a diagnosis of ovarian cancer. Alternatively, if the biomarker is down-regulated during ovarian cancer, then a measured amount below the diagnostic cutoff provides a diagnosis of ovarian cancer. As is well understood in the art, by adjusting the particular diagnostic cut-off used in an assay, one can increase sensitivity or specificity of the diagnostic assay depending on the preference of the diagnostician. The particular diagnostic cut-off can be determined, for example, by measuring the amount of the biomarker in a statistically significant number of samples from subjects with the different ovarian cancer statuses, as was done here, and drawing the cut-off to suit the diagnostician's desired levels of specificity and sensitivity.

Combinations of Markers

While individual biomarkers are useful diagnostic biomarkers, it has been found that a combination of biomarkers can provide greater predictive value of a particular status than single biomarkers alone. Specifically, the detection of a plurality of biomarkers in a sample can increase the sensitivity and/or specificity of the test. A combination of at least two biomarkers is sometimes referred to as a "biomarker profile" or "biomarker fingerprint." A combination of the biomarkers set forth in Tables 1, 3 and 4 can be detected. Similarly, one or more of the biomarkers set forth in Tables 1, 3 and 4 can be detected in combination with other known ovarian cancer biomarkers, such as CA125. Examples of known ovarian cancer biomarkers useful in combination with the biomarkers of the present invention include, but are not limited to, those set forth in PCT Publications Nos. WO 03/057014 and WO 2004/012588, both of which are incorporated herein by reference for all purposes.

The protocols described in the Examples below were used to generate mass spectra from 65 patient samples, 30 of which were diagnosed with ovarian cancer and 35 of which did not exhibit ovarian cancer. The peak masses and heights were abstracted into a discovery data set. This data set was used to train a learning algorithm employing classification and regression tree analysis (CART) (Ciphergen Biomarker Patterns Software™). In particular, CART chose many subsets of the peaks at random. For each subset, CART generated a best or near best decision tree to classify a sample as ovarian cancer (malignant), ovarian cancer LMP, benign ovarian disease or other malignant condition. Among the many decision trees generated by CART, several had excellent sensitivity and specificity in distinguishing ovarian cancer (malignant, such as invasive epithelial ovarian cancer) from ovarian cancer of low malignant potential versus benign ovarian disease.

It is also noted that the specifics of the decision trees, in particular the cut-off values used in making branching decisions, depends on the details of the assay used to generate the discovery data set. The data acquisition parameters of the assay that produced the data used in the present analysis is provided in the Example. In developing a classification algorithm from, for example, a new sample set or a different assay protocol, the operator uses a protocol that detects these biomarkers and keys the learning algorithm to include them.

Also, a diagnostic test for ovarian cancer status involving the measurement of any biomarker of this invention in combination with any of the following biomarkers for ovarian cancer identified in Table 2 (including their modified forms where appropriate):

TABLE 2

| Marker | Comments (up- or down-regulated in cancer) |
|---|---|
| CTAP3 | Up-regulated; 9293D IMAC-Cu 100 mM Na phosphate, pH 7.0 |
| Transferrin | Down-regulated; 79 kD, detected on IMAC ProteinChip array charged with nickel WO 03/057014 |
| Haptoglobin precursor protein fragment | Up-regulated; 9.2 kD detected on IMAC ProteinChip array charged with nickel WO 03/057014 |
| ApoA1 | Down-regulated; predicted mass 28078.62D; detected on IMAC or H50 ProteinChip array. WO 2004/013609 |
| Transthyretin and transthyretin delta N 10 | Down-regulated; predicted mass 13761D and 12887 D, respectively; detected on Q10 ProteinChip array. WO 2004/013609 |
| ITIH4 internal fragments | Up-regulated; among other fragments: MNFRPGVLSSRQLGLPGPPDVPDHAAYHPF (SEQ ID NO: 1), a fragment spanning amino acids 660-689 of human Inter-alpha trypsin inhibitor, heavy chain H4, predicted mass: 3273.72 D; detected on IMAC ProteinChip array WO 2004/013609 and WO 2005/098447 |

TABLE 2-continued

| Marker | Comments (up- or down-regulated in cancer) |
|---|---|
| Beta 2-microglobulin | Up-regulated; detected at 11.7 KD on IMAC-Cu ProteinChip array<br>U.S. Provisional Application No. 60/693,679, filed Jun. 24, 2005 |
| Hepcidin and modified forms | Up-regulated; detected by SELDI - co-precipitate with ITIH4 fragment.<br>Hepcidin-25 (SEQ ID NO: 2): DTHFPICIFCCGCCHRSKCGMCCKT<br>Hepcidin-24 (SEQ ID NO: 3): THFPICIFCCGCCHRSKCGMCCKT<br>Hepcidin-22 (SEQ ID NO: 3): FPICIFCCGCCHRSKCGM CCKT<br>Hepcidin-20 (SEQ ID NO: 4): ICIFCCGCCHRSKCGMCCKT |
| Haptoglobin alpha | Up-regulated. Detected at 11,600D-11,700D on an IMAC ProteinChip array charged with copper;<br>WO 02/100242 |
| Prostatin | Up-regulated<br>U.S. Pat. No. 6,846,642 |
| Osteopontin | Up-regulated<br>In urine - Glycosylated -- US 2005-0009120 A1<br>In serum - US 2005-0214826 |
| Eosinophil-derived neurotoxin | Up regulated in urine. Glycosylated Detected at 17.4 KDa on a WCX2 ProteinChip array.<br>US 2005-0009120 A1 |
| leptin | Down-regulated;<br>US 2005-0214826 |
| prolactin | Up-regulated;<br>US 2005-0214826 |
| IGF-II | Down-regulated;<br>US 2005-0214826 |
| Hemoglobin (alpha-hemoglobin, beta-hemoglobin) | Up-regulated;<br>WO 2006-019906 |
| CA 125 | Up-regulated |

Other biomarkers with which the biomarkers of the present invention can be combined include, but are not limited to, CTAP3, CA125 II, CA15-3, CA19-9, CA72-4, CA 195, tumor associated trypsin inhibitor (TATI), CEA, placental alkaline phosphatase (PLAP), Sialyl TN, galactosyltransferase, macrophage colony stimulating factor (M-CSF, CSF-1), lysophosphatidic acid (LPA), 110 kD component of the extracellular domain of the epidermal growth factor receptor (p110EGFR), tissue kallikreins, e.g., kallikrein 6 and kallikrein 10 (NES-1), prostasin, HE4, creatine kinase B (CKB), LASA, HER-2/neu, urinary gonadotropin peptide, Dianon NB 70/K, Tissue peptide antigen (TPA), SMRP, osteopontin, and haptoglobin, leptin, prolactin, insulin like growth factor I or II.

Ovarian Cancer Status

Determining ovarian cancer status typically involves classifying an individual into one of two or more groups (statuses) based on the results of the diagnostic test. The diagnostic tests described herein can be used to classify between a number of different states.

Presence of Ovarian Cancer

In one embodiment, this invention provides methods for determining the presence of ovarian cancer in a subject (status: ovarian cancer versus ovarian cancer of low malignant potential or benign ovarian disease). The presence or absence of ovarian cancer is determined by measuring the relevant biomarker or biomarkers and then either submitting them to a classification algorithm or comparing them with a reference amount and/or pattern of biomarkers that is associated with the particular risk level.

Determining Risk of Developing Disease

In one embodiment, this invention provides methods for determining the risk of developing disease in a subject. Biomarker amounts or patterns are characteristic of various risk states, e.g., high, medium or low. The risk of developing a disease is determined by measuring the relevant biomarker or biomarkers and then either submitting them to a classification algorithm or comparing them with a reference amount and/or pattern of biomarkers that is associated with the particular risk level.

Determining Stage of Disease

In one embodiment, this invention provides methods for determining the stage of disease in a subject. Each stage of the disease has a characteristic amount of a biomarker or relative amounts of a set of biomarkers (a pattern). The stage of a disease is determined by measuring the relevant biomarker or biomarkers and then either submitting them to a classification algorithm or comparing them with a reference amount and/or pattern of biomarkers that is associated with the particular stage. For example, one can classify between early stage ovarian cancer and non-ovarian cancer or among stage I ovarian cancer, stage II ovarian cancer and stage III ovarian cancer.

Determining Course (Progression/Remission) of Disease

In one embodiment, this invention provides methods for determining the course of disease in a subject. Disease course refers to changes in disease status over time, including disease progression (worsening) and disease regression (improvement). Over time, the amounts or relative amounts (e.g., the pattern) of the biomarkers changes. Therefore, the trend of these markers, either increased or decreased over time toward diseased or non-diseased indicates the course of the disease. Accordingly, this method involves measuring one or more biomarkers in a subject at least two different time points, e.g., a first time and a second time, and comparing the change in amounts, if any. The course of disease is determined based on these comparisons.

Similarly, changes in the rate of disease progression (or regression) may be monitored by measuring the amount of a biomarker, e.g., a peptide biomarkers of Table 1, at different times and calculating the rate of change in biomarker levels. The ability to measure disease state or velocity of disease progression can be important for drug treatment studies where the goal is to slow down or arrest disease progression through therapy.

Reporting the Status

Additional embodiments of the invention relate to the communication of assay results or diagnoses or both to technicians, physicians or patients, for example. In certain embodiments, computers will be used to communicate assay results or diagnoses or both to interested parties, e.g., physicians and their patients. In some embodiments, the assays will be performed or the assay results analyzed in a country or jurisdiction which differs from the country or jurisdiction to which the results or diagnoses are communicated.

In a preferred embodiment of the invention, a diagnosis based on the differential presence in a test subject of any of the peptide biomarkers of Tables 1, 3 or 4 is communicated to the subject as soon as possible after the diagnosis is obtained. The diagnosis may be communicated to the subject by the subject's treating physician. Alternatively, the diagnosis may be sent to a test subject by email or communicated to the subject by phone. A computer may be used to communicate the diagnosis by email or phone. In certain embodiments, the message containing results of a diagnostic test may be generated and delivered automatically to the subject using a combination of computer hardware and software which will be familiar to artisans skilled in telecommunications. One example of a healthcare-oriented communications system is described in U.S. Pat. No. 6,283,761; however, the present invention is not limited to methods which utilize this particular communications system. In certain embodiments of the methods of the invention, all or some of the method steps, including the assaying of samples, diagnosing of diseases, and communicating of assay results or diagnoses, may be carried out in diverse (e.g., foreign) jurisdictions.

Subject Management

In certain embodiments of the methods of qualifying ovarian cancer status, the methods further comprise managing subject treatment based on the status. Such management includes the actions of the physician or clinician subsequent to determining ovarian cancer status. For example, if a physician makes a diagnosis of ovarian cancer, then a certain regime of treatment, such as prescription or administration of an anti-chemotherapeutic agent might follow. Alternatively, a diagnosis of ovarian cancer LMP or benign ovarian disease might be followed with further testing to determine a specific disease that might the patient might be suffering from. Also, if the diagnostic test gives an inconclusive result on ovarian cancer status, further tests may be called for.

Additional embodiments of the invention relate to the communication of assay results or diagnoses or both to technicians, physicians or patients, for example. In certain embodiments, computers will be used to communicate assay results or diagnoses or both to interested parties, e.g., physicians and their patients. In some embodiments, the assays will be performed or the assay results analyzed in a country or jurisdiction which differs from the country or jurisdiction to which the results or diagnoses are communicated.

In a preferred embodiment of the invention, a diagnosis based on the presence or absence in a test subject of any the biomarkers of Table 1 is communicated to the subject as soon as possible after the diagnosis is obtained. The diagnosis may be communicated to the subject by the subject's treating physician. Alternatively, the diagnosis may be sent to a test subject by email or communicated to the subject by phone. A computer may be used to communicate the diagnosis by email or phone. In certain embodiments, the message containing results of a diagnostic test may be generated and delivered automatically to the subject using a combination of computer hardware and software which will be familiar to artisans skilled in telecommunications. One example of a healthcare-oriented communications system is described in U.S. Pat. No. 6,283,761; however, the present invention is not limited to methods which utilize this particular communications system. In certain embodiments of the methods of the invention, all or some of the method steps, including the assaying of samples, diagnosing of diseases, and communicating of assay results or diagnoses, may be carried out in diverse (e.g., foreign) jurisdictions.

VI. Determining Therapeutic Efficacy of Pharmaceutical Drug

In another embodiment, this invention provides methods for determining the therapeutic efficacy of a pharmaceutical drug. These methods are useful in performing clinical trials of the drug, as well as monitoring the progress of a patient on the drug. Therapy or clinical trials involve administering the drug in a particular regimen. The regimen may involve a single dose of the drug or multiple doses of the drug over time. The doctor or clinical researcher monitors the effect of the drug on the patient or subject over the course of administration. If the drug has a pharmacological impact on the condition, the amounts or relative amounts (e.g., the pattern or profile) of the biomarkers of this invention changes toward a non-disease profile. For example, biomarkers ApoCI and hemoglobin are increased with disease, while biomarker M32600 is decreased in disease. Therefore, one can follow the course of the amounts of these biomarkers in the subject during the course of treatment. Accordingly, this method involves measuring one or more biomarkers in a subject receiving drug therapy, and correlating the amounts of the biomarkers with the disease status of the subject. One embodiment of this method involves determining the levels of the biomarkers at at least two different time points during a course of drug therapy, e.g., a first time and a second time, and comparing the change in amounts of the biomarkers, if any. For example, the biomarkers can be measured before and after drug administration or at two different time points during drug administration. The effect of therapy is determined based on these comparisons. If a treatment is effective, then the biomarkers will trend toward normal, while if treatment is ineffective, the biomarkers will trend toward disease indications. If a treatment is effective, then the biomarkers will trend toward normal, while if treatment is ineffective, the biomarkers will trend toward disease indications.

VII. Generation of Classification Algorithms for Qualifying Ovarian Cancer Status In some embodiments, data derived from the spectra (e.g., mass spectra or time-of-flight spectra) that are generated using samples such as "known samples" can then be used to "train" a classification model. A "known sample" is a sample that has been pre-classified. The data that are derived from the spectra and are used to form the classification model can be referred to as a "training data set." Once trained, the classification model can recognize patterns in data derived from spectra generated using unknown samples. The classification model can then be used to classify the unknown samples into classes. This can be useful, for example, in predicting whether or not a particular biological sample is associated with a certain biological condition (e.g., diseased versus non-diseased).

The training data set that is used to form the classification model may comprise raw data or pre-processed data. In some embodiments, raw data can be obtained directly from time-of-flight spectra or mass spectra, and then may be optionally "pre-processed" as described above.

Classification models can be formed using any suitable statistical classification (or "learning") method that attempts to segregate bodies of data into classes based on objective parameters present in the data. Classification methods may be either supervised or unsupervised. Examples of supervised and unsupervised classification processes are described in Jain, "Statistical Pattern Recognition: A Review," *IEEE Transactions on Pattern Analysis and Machine Intelligence*, Vol. 22, No. 1, January 2000, the teachings of which are incorporated by reference.

In supervised classification, training data containing examples of known categories are presented to a learning mechanism, which learns one or more sets of relationships that define each of the known classes. New data may then be applied to the learning mechanism, which then classifies the new data using the learned relationships. Examples of supervised classification processes include linear regression processes (e.g., multiple linear regression (MLR), partial least squares (PLS) regression and principal components regression (PCR)), binary decision trees (e.g., recursive partitioning processes such as CART—classification and regression trees), artificial neural networks such as back propagation networks, discriminant analyses (e.g., Bayesian classifier or Fischer analysis), logistic classifiers, and support vector classifiers (support vector machines).

A preferred supervised classification method is a recursive partitioning process. Recursive partitioning processes use recursive partitioning trees to classify spectra derived from unknown samples. Further details about recursive partitioning processes are provided in U.S. Patent Application No. 2002/0138208 A1 to Paulse et al., "Method for Analyzing Mass Spectra."

In other embodiments, the classification models that are created can be formed using unsupervised learning methods. Unsupervised classification attempts to learn classifications based on similarities in the training data set, without pre-classifying the spectra from which the training data set was derived. Unsupervised learning methods include cluster analyses. A cluster analysis attempts to divide the data into "clusters" or groups that ideally should have members that are very similar to each other, and very dissimilar to members of other clusters. Similarity is then measured using some distance metric, which measures the distance between data items, and clusters together data items that are closer to each other. Clustering techniques include the MacQueen's K-means algorithm and the Kohonen's Self-Organizing Map algorithm.

Learning algorithms asserted for use in classifying biological information are described, for example, in PCT International Publication No. WO 01/31580 (Barnhill et al., "Methods and Devices for Identifying Patterns in Biological Systems and Methods of Use Thereof"), U.S. Patent Application No. 2002 0193950 A1 (Gavin et al., "Method or analyzing mass spectra"), U.S. Patent Application No. 2003 0004402 A1 (Hitt et al., "Process for Discriminating Between Biological States Based on Hidden Patterns from Biological Data"), and U.S. Patent Application No. 2003 0055615 A1 (Zhang et al., "Systems and Methods for Processing Biological Expression Data").

The classification models can be formed on and used on any suitable digital computer. Suitable digital computers include micro, mini, or large computers using any standard or specialized operating system, such as a Unix, Windows™ or Linux™ based operating system. The digital computer that is used may be physically separate from the mass spectrometer that is used to create the spectra of interest, or it may be coupled to the mass spectrometer.

The training data set and the classification models according to embodiments of the invention can be embodied by computer code that is executed or used by a digital computer. The computer code can be stored on any suitable computer readable media including optical or magnetic disks, sticks, tapes, etc., and can be written in any suitable computer programming language including C, $C^{++}$, visual basic, etc.

The learning algorithms described above are useful both for developing classification algorithms for the biomarkers already discovered, or for finding new biomarkers for ovarian cancer. The classification algorithms, in turn, form the base for diagnostic tests by providing diagnostic values (e.g., cut-off points) for biomarkers used singly or in combination.

VIII. Use of Biomarkers for Imaging

Non-invasive medical imaging techniques such as Positron Emisson Tomography (PET) or single photon emission computerized tomography (SPECT) imaging are particularly useful for the detection of cancer, coronary artery disease and brain disease. PET and SPECT imaging shows the chemical functioning of organs and tissues, while other imaging techniques—such as X-ray, CT and MRI—show structure. The use of PET and SPECT imaging has become increasingly useful for qualifying and monitoring the development of brain diseases such as Alzheimer's disease. In some instances, the use of PET or SPECT imaging allows Alzheimer's disease to be detected several years earlier than the onset of symptoms. See, e.g., Vassaux and Groot-wassink, "In Vivo Noninvasive Imaging for Gene Therapy," J. Biomedicine and Biotechnology, 2: 92-101 (2003).

Different strategies are being used to develop compounds suitable for in vivo imaging of amyloid deposits in human brains. Monoclonal antibodies against A-beta and peptide fragments have had limited uptake by the brain when tested in patients with AD. The small molecular approach for amyloid imaging has so far been most successful, as described by, e.g., Nordberg A, Lancet Neurol., 3(9):519-27 (2004); Kung MP et al, Brain Res., 1025(1-2):98-105 (2004); Herholz K et al., Mol Imaging Biol., 6(4):239-69 (2004); Neuropsychol Rev., Zakzanis K K et al., 13(1):1-18 (2003); Herholz K, Ann Nucl Med., 17(2):79-89 (2003).

The peptide biomarkers disclosed herein, or fragments thereof, can be used in the context of PET and SPECT imaging applications. After modification with appropriate tracer residues for PET or SPECT applications, peptide biomarkers which interact with amyloid plaque proteins can be used to image the deposition of amyloid plaques in Alzheimer's patients.

Antisense technology may be used to detect expression of transcripts whose translation is correlated with the biomarkers identified herein. For example, the use of antisense peptide nucleic acid (PNA) labeled with an appropriate radionuclide, such as $^{111}$In, and conjugated to a brain drug-targeting system to enable transport across biologic membrane barriers, has been demonstrated to allow imaging of endogenous gene expression in brain cancer. See Suzuki et al., Journal of Nuclear Medicine, 10:1766-1775 (2004). Suzuki et al. utilize a delivery system comprising monoclonal antibodies that target transferring receptors at the blood-brain barrier and facilitate transport of the PNA across that barrier.

IX. Compositions of Matter

In another aspect, this invention provides compositions of matter based on the biomarkers of this invention.

In one embodiment, this invention provides biomarkers of this invention in purified form. Purified biomarkers have utility as antigens to raise antibodies. Purified biomarkers also have utility as standards in assay procedures. As used herein, a "purified biomarker" is a biomarker that has been isolated from other proteins and peptides, and/or other material from the biological sample in which the biomarker is found. Biomarkers may be purified using any method known in the art, including, but not limited to, mechanical separation (e.g., centrifugation), ammonium sulphate precipitation, dialysis (including size-exclusion dialysis), size-exclusion chromatography, affinity chromatography, anion-exchange chromatography, cation-exchange chromatography, and methal-chelate chromatography. Such methods may be performed at any appropriate scale, for example, in a chromatography column, or on a biochip.

In another embodiment, this invention provides a biospecific capture reagent, optionally in purified form, that specifically binds a biomarker of this invention. In one embodiment, the biospecific capture reagent is an antibody. Such compositions are useful for detecting the biomarker in a detection assay, e.g., for diagnostics.

In another embodiment, this invention provides an article comprising a biospecific capture reagent that binds a biomarker of this invention, wherein the reagent is bound to a solid phase. For example, this invention contemplates a device comprising bead, chip, membrane, monolith or microtiter plate derivatized with the biospecific capture reagent. Such articles are useful in biomarker detection assays.

In another aspect this invention provides a composition comprising a biospecific capture reagent, such as an antibody, bound to a biomarker of this invention, the composition optionally being in purified form. Such compositions are useful for purifying the biomarker or in assays for detecting the biomarker.

In another embodiment, this invention provides an article comprising a solid substrate to which is attached an adsorbent, e.g., a chromatographic adsorbent or a biospecific capture reagent, to which is further bound a biomarker of this invention. In one embodiment, the article is a biochip or a probe for mass spectrometry, e.g., a SELDI probe. Such articles are useful for purifying the biomarker or detecting the biomarker.

X. Kits for Detection of Biomarkers for Ovarian Cancer

In another aspect, the present invention provides kits for qualifying ovarian cancer status, which kits are used to detect biomarkers according to the invention. In one embodiment, the kit comprises a solid support, such as a chip, a microtiter plate or a bead or resin having a capture reagent attached thereon, wherein the capture reagent binds a biomarker of the invention. Thus, for example, the kits of the present invention can comprise mass spectrometry probes for SELDI, such as ProteinChip® arrays. In the case of biospecific capture reagents, the kit can comprise a solid support with a reactive surface, and a container comprising the biospecific capture reagent.

The kit can also comprise a washing solution or instructions for making a washing solution, in which the combination of the capture reagent and the washing solution allows capture of the biomarker or biomarkers on the solid support for subsequent detection by, e.g., mass spectrometry. The kit may include more than type of adsorbent, each present on a different solid support.

In a further embodiment, such a kit can comprise instructions for suitable operational parameters in the form of a label or separate insert. For example, the instructions may inform a consumer about how to collect the sample, how to wash the probe or the particular biomarkers to be detected.

In yet another embodiment, the kit can comprise one or more containers with biomarker samples, to be used as standard(s) for calibration.

XI. Use of Biomarkers for Ovarian Cancer in Screening Assays and Methods of Treating Ovarian Cancer The methods of the present invention have other applications as well. For example, the biomarkers can be used to screen for compounds that modulate the expression of the biomarkers in vitro or in vivo, which compounds in turn may be useful in treating or preventing ovarian cancer in patients. In another example, the biomarkers can be used to monitor the response to treatments for ovarian cancer. In yet another example, the biomarkers can be used in heredity studies to determine if the subject is at risk for developing ovarian cancer.

Thus, for example, the kits of this invention could include a solid substrate having a hydrophobic function, such as a protein biochip (e.g., a Ciphergen H50 ProteinChip array, e.g., ProteinChip array) and a sodium acetate buffer for washing the substrate, as well as instructions providing a protocol to measure the biomarkers of this invention on the chip and to use these measurements to diagnose ovarian cancer.

Compounds suitable for therapeutic testing may be screened initially by identifying compounds which interact with one or more biomarkers listed in Tables 1, 3 and 4. By way of example, screening might include recombinantly expressing a biomarker listed in Tables 1, 3 or 4, purifying the biomarker, and affixing the biomarker to a substrate. Test compounds would then be contacted with the substrate, typically in aqueous conditions, and interactions between the test compound and the biomarker are measured, for example, by measuring elution rates as a function of salt concentration. Certain proteins may recognize and cleave one or more biomarkers of Tables 1, 3 and 4, in which case the proteins may be detected by monitoring the digestion of one or more biomarkers in a standard assay, e.g., by gel electrophoresis of the proteins.

In a related embodiment, the ability of a test compound to inhibit the activity of one or more of the biomarkers of Tables 1, 3 and 4 may be measured. One of skill in the art will recognize that the techniques used to measure the activity of a particular biomarker will vary depending on the function and properties of the biomarker. For example, an enzymatic activity of a biomarker may be assayed provided that an appropriate substrate is available and provided that the concentration of the substrate or the appearance of the reaction product is readily measurable. The ability of potentially therapeutic test compounds to inhibit or enhance the activity of a given biomarker may be determined by measuring the rates of catalysis in the presence or absence of the test compounds. The ability of a test compound to interfere with a non-enzymatic (e.g., structural) function or activity of one of the biomarkers of Tables 1, 3 and 4 may also be measured. For example, the self-assembly of a multi-protein complex which includes one of the biomarkers of Tables 1, 3 and 4 may be monitored by spectroscopy in the presence or absence of a test compound. Alternatively, if the biomarker is a non-enzymatic enhancer of transcription, test compounds which interfere with the ability of the biomarker to enhance transcription may be identified by measuring the levels of biomarker-dependent transcription in vivo or in vitro in the presence and absence of the test compound.

Test compounds capable of modulating the activity of any of the biomarkers of Tables 1, 3 and 4 may be administered to patients who are suffering from or are at risk of developing ovarian cancer or other cancer. For example, the administration of a test compound which increases the activity of a particular biomarker may decrease the risk of ovarian cancer in a patient if the activity of the particular biomarker in vivo prevents the accumulation of proteins for ovarian cancer. Conversely, the administration of a test compound which decreases the activity of a particular biomarker may decrease the risk of ovarian cancer in a patient if the increased activity of the biomarker is responsible, at least in part, for the onset of ovarian cancer.

In an additional aspect, the invention provides a method for identifying compounds useful for the treatment of disorders such as ovarian cancer which are associated with increased levels of modified forms of Calgranulin C. For example, in one embodiment, cell extracts or expression libraries may be screened for compounds which catalyze the cleavage of full-length Calgranulin C (M10430) to truncated forms of Calgranulin C (M10210). In one embodiment of such a screening assay, cleavage of Calgranulin C may be detected by attaching a fluorophore to Calgranulin C which remains quenched when Calgranulin C is uncleaved, but which fluoresces when the protein is cleaved. Alternatively, a version of full-length Calgranulin C modified so as to render the amide bond between amino acids x and y uncleavable may be used to selectively bind or "trap" the cellular protesase which cleaves full-length Calgranulin C at that site in vivo. Methods for screening and identifying proteases and their targets are well-documented in the scientific literature, e.g., in Lopez-Ottin et al. (*Nature Reviews*, 3:509-519 (2002)).

In yet another embodiment, the invention provides a method for treating or reducing the progression or likelihood of a disease, e.g., ovarian cancer, which is associated with the increased levels of truncated Calgranulin C. For example, after one or more proteins have been identified which cleave full-length Calgranulin C, combinatorial libraries may be screened for compounds which inhibit the cleavage activity of the identified proteins. Methods of screening chemical libraries for such compounds are well-known in art. See, e.g., Lopez-Otin et al. (2002). Alternatively, inhibitory compounds may be intelligently designed based on the structure of Calgranulin C.

At the clinical level, screening a test compound includes obtaining samples from test subjects before and after the subjects have been exposed to a test compound. The levels in the samples of one or more of the biomarkers listed in Tables 1, 3 and 4 may be measured and analyzed to determine whether the levels of the biomarkers change after exposure to a test compound. The samples may be analyzed by mass spectrometry, as described herein, or the samples may be analyzed by any appropriate means known to one of skill in the art. For example, the levels of one or more of the biomarkers listed in Tables 1, 3 and 4 may be measured directly by Western blot using radio- or fluorescently-labeled antibodies which specifically bind to the biomarkers. Alternatively, changes in the levels of mRNA encoding the one or more biomarkers may be measured and correlated with the administration of a given test compound to a subject. In a further embodiment, the changes in the level of expression of one or more of the biomarkers may be measured using in vitro methods and materials. For example, human tissue cultured cells which express, or are capable of expressing, one or more of the biomarkers of Tables 1, 3 and 4 may be contacted with test compounds. Subjects who have been treated with test compounds will be routinely examined for any physiological effects which may result from the treatment. In particular, the test compounds will be evaluated for their ability to decrease disease likelihood in a subject. Alternatively, if the test compounds are administered to subjects who have previously been diagnosed with ovarian cancer, test compounds will be screened for their ability to slow or stop the progression of the disease.

XII. Examples

Example 1

Discovery of Biomarkers for Ovarian Cancer

Samples:
Ovarian cyst fluid samples were acquired from the University of Kentucky. The samples had been collected from patients intra-operatively and stored at −80° C. Sample distribution was as follows: invasive epithelial ovarian cancer (OvCa), 12; low malignant potential (borderline), 13; other malignancies, 6; and benign, 39.

Samples: Serum Profiling:
Ovarian cyst profiling was performed using both direct chip binding procedures as well as anion exchange fractionation followed by chip binding procedures. Randomized templates containing the samples to be profiled were generated using the Ciphergen Express software program. Samples were thawed on ice, added to a 96 well-plate (following the template for arrangement), and centrifuged for 20 minutes at 4000 rpm. Aliquots of the cyst fluid were then put into fresh 96 well-plates and stored at −80° C. until use. Serum samples were profiled on IMAC-$Cu^{++}$ on Oct. 6, 2004 and on Q10 on Oct. 14, 2004 (see, protocol below) on triplicate ProteinChip Arrays. All replicates were prepared on the same day and were read on a PCS4000. Arrays were processed with sample using a Biomek 2000 or Tecan Aquarius robot.

Direct Chip Binding Protocol:
1. 5 µl sample was denatured with 7.5 µl U9 buffer.
2. Shake at 4° C. for 20 minutes.
3. Added 112.5 µl 50 mM tris, pH9 buffer to make final volume as 125 µl.
4. 5 µl of this denature sample was applied to all four chip types.

Chip Binding:
IMAC30: IMAC30 ProteinChip arrays were coupled with copper. The binding and washing buffer was 50 mM Tris pH 8.0/500 mM NaCl.
CM10: The binding and washing buffer was 100 mM NaAcetate pH 4.0.
H50: The binding and washing buffer was 10% acetonitrile buffer.
Q10: The binding and washing buffer was 50 mM tris buffer at pH8.0.
Binding time: 60 minutes at room temperature.

Matrix was Sinapinic Acid.

1. Anion Exchange Fractionation Protocol:

Buffer List:
1. U9 (9 M urea, 2% CHAPS, 50 mM Tris-HCl pH9).
2. U1 (1 M urea, 0.22% CHAPS, 50 mM Tris-HCl pH9).
3. 50 mM Tris-HCl with 0.1% OGP pH9 (Wash buffer 1).
4. 50 mM Hepes with 0.1% OGP pH7 (Wash buffer 2).
5. 100 mM NaAcetate with 0.1% OGP pH5 (Wash buffer 3).
6. 100 mM NaAcetate with 0.1% OGP pH4 (Wash buffer 4).
7. 50 mM NaCitrate with 0.1% OGP pH3 (Wash buffer 5).
8. 33.3% isopropanol/16.7% acetonitrile/0.1% trifluoroacetic acid (Wash buffer 6).

Note: Do not aliquot wash buffer 6 into the buffer tray until wash buffer 5 is being applied to the resin. This ensures that evaporation of the volatile organic solvents will not be an issue.

Material List:
Filter plate.
6 v-well 96 well dishes, labeled F1-F6.

A. Wash Resin

Prepare resin by washing Hyper Q DF resin 3 times with 5 bed volumes 50 mM Tris-HCl pH9. Then store in 50 mM Tris-HCl pH9 in a 50% suspension.

B. Denature Serum Protein

Thaw frozen serum and spin 20000 g for 10' at 4°.
Aliquot 20 µl serum to each well of the 96-well plate.
Add 30 µl U9 to each sample.
Vortex 20' at 4°.

C. Equilibrate Resin

Add 180 µl (240 µl for rat serum) Hyper Q DF to each well in filter plate.
Filter buffer.
Add 200 µl U1 to each well.
Filter buffer.
Add 200 µl U1 to each well.
Filter buffer.
Add 200 µl U1 to each well.
Filter buffer.

D. Bind Serum with Resin

Pipet 50 µl of sample from each well to corresponding well in filter plate.
Add 50 µl of U1 to each well of sample plate.
Mix 5 times.
Pipet 50 µl from each well of sample plate to corresponding well in filter plate.
[This step is included because there is a dead volume when pipeting with the robot; when the robot pipets to collect the sample the first time, it will not collect all the material. The addition of 50 µl U1 and mixing allows the residual material to be obtained and added to the first 50 µl.]
Vortex 30' at 4°

E. Collect Fractions

Place v-well 96 well plate F1 under filter plate.
  Collect flow-through in plate F1.
Add 100 µl of wash buffer 1 to each well of filter plate.
Vortex 10' at Room Temperature (RT).
  Collect pH 9 eluant in plate F1.
  Fraction 1 contains the flow through and the pH 9 eluant.
Add 100 µl of wash buffer 2 to each well of filter plate.
Vortex 10' at Room Temperature (RT).
Place v-well 96 well plate F2 under filter plate.
  Collect fraction 2 in plate F2.
Add 100 µl of wash buffer 2 to each well of filter plate.
Vortex 10' at Room Temperature (RT).
  Collect remainder of fraction 2 in plate F2.
  Fraction 2 contains the pH 7 eluant.
Add 100 µl of wash buffer 3 to each well of filter plate.
Vortex 10' at Room Temperature (RT).
Place v-well 96 well plate F3 under filter plate.
  Collect fraction 3 in plate F3.
Add 100 µl of wash buffer 3 to each well of filter plate.
Vortex 10' at Room Temperature (RT).
  Collect remainder of fraction 3 in plate F3.
  Fraction 3 contains the pH 5 eluant.
Add 100 µl of wash buffer 4 to each well of filter plate.
Vortex 10' at Room Temperature (RT).
Place v-well 96 well plate F4 under filter plate.
  Collect fraction 4 in plate F4.
Add 100 µl of wash buffer 4 to each well of filter plate.
Vortex 10' at Room Temperature (RT).
  Collect remainder of fraction 4 in plate F4.
  Fraction 4 contains the pH 4 eluant.
Add 100 µl of wash buffer 5 to each well of filter plate.
Vortex 10' at Room Temperature (RT).
Place v-well 96 well plate F5 under filter plate.
  Collect fraction 5 in plate F5.
Add 100 µl of wash buffer 5 to each well of filter plate.
Vortex 10' at Room Temperature (RT).
  Collect remainder of fraction 5 in plate F5.
  Fraction 5 contains the pH 3 eluant.
Add 100 µl of wash buffer 6 to each well of filter plate.
Vortex 10' at Room Temperature (RT).
Place v-well 96 well plate F6 under filter plate.
  Collect fraction 6 in plate F6.
Add 100 µl of wash buffer 6 to each well of filter plate.
Vortex 10' at Room Temperature (RT).
  Collect remainder of fraction 6 in plate F6.
  Fraction 6 contains the organic solvent eluant.
Freeze until proceeding with chip binding protocol.

Chip Binding Protocol

Buffer List:
IMAC30 Chip:
1. 100 mM Sodium Phosphate+0.5M NaCl pH 7.0.
2. 100 mM $CuSO_4$.
3. 100 mM NaAcetate pH 4.0.
CM10 Chip:
1. 100 mM Sodium Acetate pH 4.0

Material List:
Bioprocessors.
IMAC30 chips.
CM10 chips.
Place chips into bioprocessor.

A. Load LMAC Chips with Copper

Load 50 µl of $CuSO4$ onto each spot on the EVIAC3 chip.
Centrifuge the bioprocessor at 700 rpm for 1 minutes.
Vortex 5' at Room Temperature (RT).
Remove $CuSO_4$ after Vortex.
Water rinse.

B. Neutralize IMAC Chips

Load 50 µl of NaAcetate pH 4.0 onto each spot on the IMAC3 chip.
Vortex 5' at Room Temperature (RT).
Remove NaAcetate after Vortex.
Water rinse.

C. Equilibrate Chips

Add 150 µl of appropriate chip binding buffer into each well.
Centrifuge the bioprocessor at 700 rpm for 1 minutes for CM10.
Vortex 5' at Room Temperature (RT).

Remove buffer.
Add 150 µl of appropriate buffer into each well.
Vortex 5' at Room Temperature (RT).
Remove buffer after vortex.
D. Bind Fractions to Chips
Add 90 µl of corresponding buffer into each well.
Add 10 µl of Q column fraction.
Centrifuge the bioprocessor at 700 rpm for 1 minutes for CM10.
Vortex 60' at Room Temperature (RT).
Remove sample and buffer.
E. Wash Chips
Add 150 µl of corresponding buffer into each well.
Vortex 5' at Room Temperature (RT).
Remove buffer after vortexing.
Add 150 p. 1 of corresponding buffer into each well.
Vortex 5' at Room Temperature (RT).
Remove buffer after vortexing.
Add 150 µl of corresponding buffer into each well.
Vortex 5' at Room Temperature (RT).
Remove buffer after vortexing.
Water rinse 2 times.
F. Add Matrix
Remove bioprocessor top and gasket.
Remove the water from spots with vacuum.
Allow the chips to dry 10 minutes.
Draw a circle around each spot using a pap pen.
For SPA:
    Add 400 µl of 50% ACN, 0.5% TFA to SPA tube.
    Vortex 5 minutes at RT.
    Add 1.0 µl to each spot.
    Air dry 10 minutes.
    Add 1.0 µl to each spot.
    Air dry.
Data Analysis:

Data were acquired using CiphergenExpress. Mass calibration was performed using external calibrants, intensity normalization was based on total ion current using an external normalization factor, and baseline subtraction was performed. Peak detection was performed in CiphergenExpress using the criteria that a peak must have a signal/noise ratio of 3:1 and be present in 20% of the spectra. Statistical analysis was performed in CiphergenExpress using the Mann-Whitney test (for two groups, e.g., benign versus ovarian cancer) or Kruskal-Wallis test (for multiple group comparison, e.g., benign ovarian disease versus ovarian cancer versus ovarian cancer with low malignant potential (LMP) versus other malignancies (such as malignancies other than invasive epithelial ovarian cancer, including metastatic cancer (e.g., gastric cancer frequently metastasizes to the ovary), mesothelioma, a stromal ovarian cancer, etc.

Results/Conclusions:

A four-way comparison was performed using the Kruskal-Wallis test. The four groups were benign ovarian disease, invasive epithelial ovarian cancer, borderline ovarian cancer (also called ovarian cancer with low malignant potential), and other malignancies (which include stromal ovarian tumor, metastatic disease, and uterine cancer).

The biomarkers for ovarian cancer in ovarian cyst fluid identified using the above methods are set forth in Table 1. Most notably, it has been determined that most peaks of significance are similarly up- or down-regulated based on the characteristics of malignancy (or not) of the disease. Benign disease and ovarian cancer of low malignant potential (also called borderline disease) tend to have the same distribution of peak intensity, while invasive ovarian cancer and other malignant diseases tend to have the same distribution of peak intensity. These biomarkers of the present invention can be used alone, or in conjunction with, other proteins previously identified to be important biomarkers for ovarian cancer.

Example 2

Marker Purification and ID

Biomarkers were purified using combinations of chromatographic techniques employing a range of Biosepra sorbents typically followed by SDS-PAGE. The purification schemes were monitored using a ProteinChip Reader to track biomarkers of interest. For proteins smaller than 30 kDa, intact bands of interest were extracted from gels and reanalyzed using the ProteinChip Reader to confirm their exact masses matched with the original biomarker. The gel-extracted proteins were in-solution digested with trypsin and proteins larger than 30 kDa were in-gel digested. Tryptic digests were analyzed by peptide mapping using the ProteinChip Reader and by tandem MS using a Q-STAR (Applied Biosystems) instrument fitted with a PCI-1000 ProteinChip Interface. Biomarkers smaller than 4 kDa were enriched by combinations of chromatographic techniques and identified directly by tandem MS without SDS-PAGE purification and/or trypsin digestion. In some instances (e.g., Lysozyme C) the biomarkers were identified using antibodies.

The techniques described in the preceding paragraph allowed the identification of the biomarkers of Table 1

Example 3

Discovery of Biomarkers

Methods

Protein expression profiling was performed on ovarian cyst fluids from seventy-four patients with ovarian tumors (16 malignant, 13 of low malignant potential, 45 benign) using the ProteinChip Biomarker System® (Ciphergen Biosystems), a platform for surface-enhanced laser desorption/ionization time-or-flight mass spectrometry. Ovarian cyst fluid was analyzed unfractionated, and also following anion exchange fractionation. Aliquots of each fraction were analyzed in duplicate on NP20, IMAC30, CM10, H50, and Q10 ProteinChip arrays. Ciphergen Express® software was used to identify m/z peaks and to compare peak intensity between diagnostic groups. Statistically significant differences in peak intensity between diagnostic groups were determined by Kruskal-Wallis test and ROC curve analysis.

Results

Over one hundred protein peaks from ovarian cyst fluid differed significantly in peak intensity between benign, malignant, and ovarian tumors of low malignant potential (see, Tables 2 and 3, below). Of these cyst fluid proteins, the following have been identified by MS/MS or MS/MS with immunoassay validation: Apolipoprotein C I (m/z=6520, p=0.0003), Apolipoprotein A II (m/z=8690, p=0.00006), and Apolipoprotein CII (m/z=8918, p=0.0002); Calgranulin A (m/z=10840, p=0.00001) and Calgranulin C (m/z=10430, p=0.00004); Transthyretin (doubly charged) (m/z=6880, p=0.00005); and Calcyclin (m/z=10210, p=00002).

TABLE 3

SELDI-TOF MS analyses of anion exchange fractionated cyst fluids from individual patients adsorbed to CM10 ProteinChip arrays and read at high laser intensity have identified thirty-five biomarkers that differ between patients with benign and low malignant potential tumors versus malignant epithelial ovarian tumors.

| M/Z | M/Z Std. | Fraction(s) | P-value(s) | ROC(s) |
|---|---|---|---|---|
| 2414 | 3.49 | 1, 2, 5 | 0.0085, 0.0085, 0.01263 | 0.231, 0.269, 0.25 |
| 2429 | 6.46 | 1 | 0.00407 | 0.212 |
| 3286 | 5.03 | 5 | 0.01091 | 0.731 |
| 3353 | 3.76 | 5 | 0.00850 | 0.731 |
| 3446 | 5.08 | 2, 6 | 0.01681, 0.00407 | 0.718, 0.782 |
| 3517 | 5.06 | 6 | 0.00365 | 0.782 |
| 3562 | 5.86 | 6 | 0.01263 | 0.731 |
| 4227 | 7.39 | 5 | 0.00988 | 0.250 |
| 4302 | 13.26 | 5 | 0.00034 | 0.854 |
| 4558 | 5.85 | 5 | 0.00003 | 0.878 |
| 4733 | 6.57 | 4, 5 | 0.01604, 0.01459 | 0.25, 0.269 |
| 4958 | 9.22 | 5 | 0.00430 | 0.250 |
| 6395 | 9.67 | 1, 5 | 0.0013, 0.00479 | 0.814, 0.737 |
| 6443 | 22.16 | 1, 4 | 0.02893, 0.00027 | 0.66, 0.827 |
| 6507 | 8.8 | 6 | 0.00035 | 0.814 |
| 6604 | 6.02 | 1 | 0.00075 | 0.782 |
| 7136 | 14.81 | 1 | 0.00505 | 0.744 |
| 7535 | 2.57 | 4 | 0.00003 | 0.878 |
| 7910 | 4.71 | 4 | 0.00003 | 0.897 |
| 8100 | 21.18 | 1 | 0.01391 | 0.731 |
| 8331 | 19.94 | 1 | 0.01845 | 0.692 |
| 8554 | 14.59 | 1 | 0.00767 | 0.737 |
| 10836 | 9.21 | 2, 4 | 0.02535, 0.03741 | 0.699, 0.667 |
| 11733 | 4.89 | 3 | 0.00592 | 0.288 |
| 12693 | 7.59 | 1 | 0.01038 | 0.718 |
| 13130 | 18.92 | 1 | 0.04417 | 0.673 |
| 13273 | 8.49 | 1 | 0.0043 | 0.756 |
| 13291 | 18.99 | 2 | 0.03437 | 0.699 |
| 13891 | 13.07 | 4 | 0.00003 | 0.891 |
| 15082 | 27.66 | 3 | 0.00186 | 0.75 |
| 15127 | 20.16 | 5 | 0.00208 | 0.788 |
| 15212 | 31.3 | 6 | 0.00155 | 0.788 |
| 15335 | 21.31 | 4 | 0.00003 | 0.878 |
| 15878 | 23.46 | 3, 4, 5, 6 | 0.00345, 0.00002, 0.0001, 0.00004 | 0.801, 0.897, 0.854, 0.865 |
| 15987 | 15.01 | 3, 4 | 0.00175, 0.00002 | 0.807, 0.878 |

Kruskal-Wallis P-value(s) and AUC values from ROC analyses are shown.
AUC values < 0.5 indicate that "peak intensity" was decreased in the ovarian cancer cases.

TABLE 4

SELDI-TOF MS analyses of anion exchange fractionated cyst fluids from individual patients adsorbed to CM10 ProteinChip arrays and read at low laser intensity have identified twenty-eight biomarkers that differ between patients with benign and low malignant potential tumors versus malignant epithelial ovarian tumors.

| M/Z | M/Z Std. | Fraction(s) | P-value(s) | ROC(s) |
|---|---|---|---|---|
| 3368 | 2.9 | 6 | 5.00E−05 | 0.865 |
| 3377 | 3.21 | 1, 5 | 0.0231, 0.01761 | 0.699, 0.699 |
| 3439 | 3.22 | 1, 5, 6 | 0.01681, 0.01932, 0.00196 | 0.718, 0.698, 0.788 |
| 3487 | 2.52 | 5, 6 | 0.00175, 0.00261 | 0.769, 0.788 |
| 4349 | 4.11 | 5 | 0.03901 | 0.679 |
| 4626 | 2.27 | 5 | 0.00002 | 0.878 |
| 6431 | 5.35 | 1, 4, 5, 6 | 0.00005, 0.00008, 0.00155, 0.00196 | 0.891, 0.846, 0.769, 0.56 |
| 6461 | 7.72 | 1 | 0.00185 | 0.794 |
| 6496 | 5.51 | 1 | 0.00261 | 0.775 |
| 6643 | 5.91 | 1 | 0.00004 | 0.858 |
| 6830 | 9.37 | 1 | 0.01681 | 0.698 |
| 6926 | 5.7 | 6 | 0.00001 | 0.923 |
| 7566 | 2.76 | 4 | 0.00002 | 0.878 |
| 7654 | 13.53 | 1 | 0.00505 | 0.737 |
| 7936 | 4.89 | 3, 4 | 0.00075, 0.00002 | 0.8, 0.897 |
| 8134 | 5.69 | 1 | 0.00479 | 0.75 |
| 8577 | 9.55 | 1 | 0.00479 | 0.737 |
| 9117 | 3.52 | 2 | 0.0085 | 0.288 |
| 10847 | 13.11 | 1, 2, 3, 4 | 0.00006, 0.02769, 0.03586, 0.02023 | 0.884, 0.66, 0.66, 0.724 |
| 12711 | 8 | 1 | 0.01391 | 0.72 |
| 13279 | 17.93 | 1 | 0.00233 | 0.77 |
| 13887 | 14.8 | 4 | 0.00004 | 0.891 |
| 15140 | 20.99 | 3, 4, 5, 6 | 0.00327, 0.000004, 0.0043, 0.00011 | 0.75, 0.897, 0.75, 0.846 |

TABLE 4-continued

SELDI-TOF MS analyses of anion exchange fractionated cyst fluids from individual patients adsorbed to CM10 ProteinChip arrays and read at low laser intensity have identified twenty-eight biomarkers that differ between patients with benign and low malignant potential tumors versus malignant epithelial ovarian tumors.

| M/Z | M/Z Std. | Fraction(s) | P-value(s) | ROC(s) |
|---|---|---|---|---|
| 15882 | 18.21 | 3, 4, 5, 6 | 0.00196, 0.00002, 0.001, 0.00002 | 0.762, 0.897, 0.865, 0.884 |
| 16008 | 36.66 | 3, 4 | 0.01038, 0.00003 | 0.743, 0.859 |
| 56427 | 258.02 | 5 | 0.00430 | 0.250 |
| 80273 | 443.86 | 4 | 0.00175 | 0.776 |
| 90954 | 350.62 | 6 | 0.00019 | 0.154 |

Kruskal-Wallis P-value(s) and AUC values from ROC analyses are shown.
AUC values < 0.5 indicate that "peak intensity" was decreased in the ovarian cancer cases.

CONCLUSIONS

Ovarian cyst fluid is a prolific source of diagnostic protein biomarkers for ovarian cancer. Some of these biomarker proteins are acute-phase reactants. As demonstrated herein, cyst fluid proteins is good source of biomarkers that are useful in a diagnostic test for ovarian cancer.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for qualifying ovarian cancer status in a subject comprising:
   (a) measuring Calcyclin, Calgranulin C and Hepcidin in an ovarian cyst fluid, urine, or serum sample from the subject by mass spectrometry or immunoassay to determine the presence, absence, or level of the measured Calcyclin, Calgranulin C and Hepcidin biomarkers, and
   (b) correlating the measurements of the presence, absence, or level of the measured Calcyclin, Calgranulin C and Hepcidin biomarkers with ovarian cancer status.

2. The method of claim 1, further comprising measuring and correlating at least one biomarker selected from the group consisting of: ApoC1, ApoAII, ApoCII, Calgranulin A, and Transthyretin.

3. The method of claim 1 further comprising measuring CA125.

4. The method of claim 1, wherein the Calcyclin, Calgranulin C, and Hepcidin are measured by capture on an adsorbent surface of a SELDI probe and detection by laser desorption-ionization mass spectrometry.

5. The method of claim 4, wherein the adsorbent is a member selected from the group consisting of a hydrophobic adsorbent, an anion exchange adsorbent, a cation exchange adsorbent and a metal chelate adsorbent.

6. The method of claim 4, wherein the adsorbent is a cation exchange adsorbent.

7. The method of claim 1, wherein Calcyclin and Hepcidin are measured by immunoassay.

8. The method of claim 1, wherein the sample is ovarian cyst fluid.

9. The method of claim 1, wherein the correlating is performed by a software classification algorithm.

10. The method of claim 1, wherein ovarian cancer status is selected from benign ovarian disease, ovarian cancer of low malignant potential, ovarian cancer and other malignant conditions.

11. The method of claim 1, wherein the presence of calcyclin rules out benign ovarian disease.

12. The method of claim 1, wherein the presence of calgranulin C rules out benign ovarian disease.

13. The method of claim 1, wherein the ovarian cancer status rules out the possibility of benign ovarian disease.

14. The method of claim 1, wherein the ovarian cancer status rules out the possibility of ovarian cancer and other malignant conditions.

15. The method of claim 1, further comprising: (c) managing subject treatment based on the status.

16. The method of claim 15, wherein, if the measurement correlates with ovarian cancer, then managing subject treatment comprises administering a chemotherapeutic agent to the subject.

17. The method of claim 15, further comprising: (d) measuring Calcyclin, Calgranulin C, and Hepcidin after subject management and correlating the measurement with disease progression.

18. The method of claim 1, further comprising: (c) reporting the status to the subject.

19. The method of claim 1, further comprising: (c) recording the status on a tangible medium.

* * * * *